*(12)* United States Patent
Zhao et al.

(10) Patent No.: US 8,273,329 B2
(45) Date of Patent: Sep. 25, 2012

(54) CYANINE COMPOUNDS, COMPOSITIONS INCLUDING THESE COMPOUNDS AND THEIR USE IN CELL ANALYSIS

(75) Inventors: Yumei Zhao, Nanshan (CN); Jianhui Shao, Nanshan (CN); Yang Zhao, Nanshan (CN); Ting Lei, Nanshan (CN); Bing Xu, Nanshan (CN)

(73) Assignee: Shenzhen Mindray Bio-Medical Electronics Co., Ltd., Shenzhen (CH)

( * ) Notice: Subject to any disclaimer, the term of this patent is extended or adjusted under 35 U.S.C. 154(b) by 239 days.

(21) Appl. No.: 12/826,231

(22) Filed: Jun. 29, 2010

(65) Prior Publication Data

US 2011/0159483 A1    Jun. 30, 2011

(30) Foreign Application Priority Data

Dec. 30, 2009  (CN) .......................... 2009 1 0238927

(51) Int. Cl.
*A61B 5/00*    (2006.01)
*A61B 8/00*    (2006.01)
*A61B 10/00*   (2006.01)
*C07D 209/02*  (2006.01)

(52) U.S. Cl. ........................................ 424/9.6; 548/455
(58) Field of Classification Search ............... 424/9.6; 548/455
See application file for complete search history.

(56) References Cited

U.S. PATENT DOCUMENTS

| 5,155,044 | A |   | 10/1992 | Ledis et al. |
| 5,298,426 | A |   | 3/1994  | Inami et al. |
| 5,518,928 | A |   | 5/1996  | Cremins et al. |
| 5,538,893 | A |   | 7/1996  | Sakata et al. |
| 5,559,037 | A |   | 9/1996  | Kim et al. |
| 5,618,733 | A | * | 4/1997  | Sakata et al. ............... 436/17 |
| 5,677,183 | A |   | 10/1997 | Takarada |
| 5,874,310 | A |   | 2/1999  | Li et al. |
| 6,197,851 | B1| * | 3/2001  | Maxwell et al. ............ 524/88 |
| 6,664,110 | B1|   | 12/2003 | Tsuji et al. |
| 2002/0022004 | A1 | * | 2/2002 | Licha et al. ................ 424/9.6 |
| 2005/0208534 | A1 |   | 9/2005 | Dallwig et al. |
| 2006/0275801 | A1 | * | 12/2006 | Henkin et al. ............ 435/6 |
| 2006/0292658 | A1 |   | 12/2006 | Lynch |
| 2010/0112584 | A1 |   | 5/2010 | Shao et al. |

FOREIGN PATENT DOCUMENTS

| CN | 1863889 | 9/2004 |
| CN | 1637077 | 12/2004 |
| CN | 1939978 | 9/2005 |
| WO | WO2008040994 | 4/2008 |

OTHER PUBLICATIONS

Dimitriev, J. Molecular Liquids, 2005, 120, p. 131-133.*
Tatarets et al., "Synthesis of Water-Soluble, Ring-Substituted Squaraine Dyes and Their Evaluation as Fluorescent Probes and Labels." Analytica Chinica Acta 570 (2006), pp. 214-223. Available on-line at www.sciencedirect.com.

* cited by examiner

*Primary Examiner* — Michael G Hartley
*Assistant Examiner* — Leah Schlientz
(74) *Attorney, Agent, or Firm* — Kory D. Christensen; Stoel Rives LLP

(57) ABSTRACT

A compound having the general formula I or a conjugate thereof, wherein various groups are as defined in the specification. A composition includes: (i) a compound having the general formula I or a conjugate thereof; and (ii) at least one surfactant selected from cationic surfactants and nonionic surfactants. Also disclosed is a preparation method for the composition and a kit comprising the composition. Further disclosed is a method for identifying and differentiating erythroblasts, basophils and lymphocytes simultaneously using the composition according to the present disclosure.

27 Claims, 7 Drawing Sheets

Formula I

CYANINE COMPOUNDS, COMPOSITIONS INCLUDING THESE COMPOUNDS AND THEIR USE IN CELL ANALYSIS

CROSS REFERENCE TO RELATED APPLICATIONS

This application claims priority to Chinese Patent Application No. 200910238927.8, filed Dec. 30, 2009, for "CYANINE COMPOUNDS, COMPOSITIONS INCLUDING THESE COMPOUNDS AND THEIR USE IN CELL ANALYSIS," the disclosure of which is fully incorporated herein by reference.

TECHNICAL FIELD

The present disclosure relates to the field of fluorescent dye compounds, more particularly to cyanine compounds.

DETAILED DESCRIPTION

Figure 1:
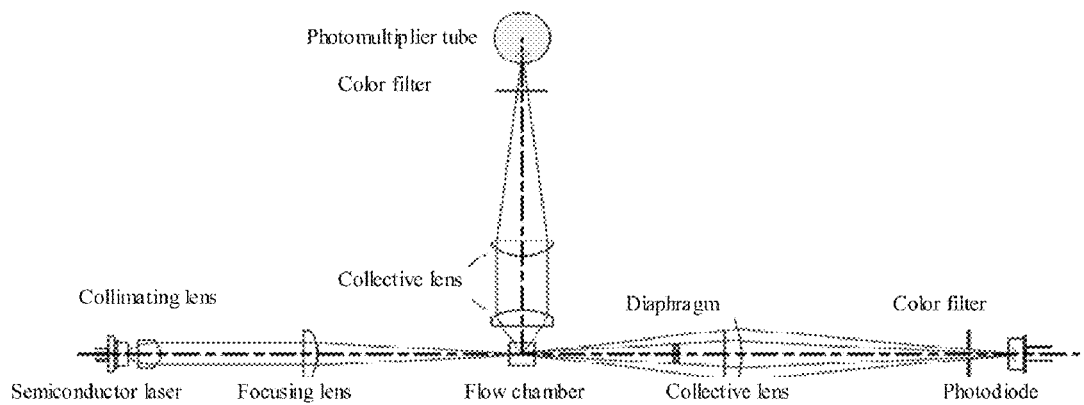
FIG. 1 is a schematic diagram of an exemplary optical system of a flow cytometer used in the analysis method in the examples of the present disclosure.

The present disclosure relates to fluorescent dyes. More particularly, the present disclosure relates to cyanine compounds applicable to staining biological samples, compositions comprising said cyanine compounds, and the method of identifying erythroblasts and differentiating and counting leucocytes using the said compositions Nucleated red blood cells (NRBC), as immature red blood cells, exist in bone marrow. It is normal that a small number of fetal erythroblasts are found in blood of a baby who is one week old. However, immature red blood cells all exist in the bone marrow of adults. It is a pathological phenomenon if immature red blood cells are found in peripheral blood. The occurrence of erythroblasts in the peripheral blood of adults is associated with various pathological states, such as hemolytic anemia, acute mass blood loss, acute histanoxia, acute and chronic leukemia, malignant tumor, myelofibrosis, etc.

In a normal person's body, there is a small amount of basophils (Baso), which is only 0-1% of leukocytes, and lymphocytes (Lym) are about 20-40% of leukocytes. Changes in the amount of these cells may be important to the diagnosis of some diseases. For example, the amount of basophils will distinctly increase in some diseases such as heavy metal poisoning, Hodgkin's disease, or chronic myeloid leukemia. Lymphocytes will increase in some diseases such as pertussis, infectious mononucleosis, chronic lymphocytic leukemia, measles, tuberculosis or hepatitis.

Therefore, it may be of clinical importance to accurately count erythroblasts, basophils and lymphocytes. Conventionally, these cells are manually counted using some chemical dyes, for example, the Wright-Giemsa staining method. These methods only provide the percentage result, need long operation time and the result is easily affected by subjective judgment of the observer, so they are not suitable for clinical test of large-scale specimens.

At present, some methods for analysis of erythroblasts and leucocyte subgroups had been reported. Basically, in these methods erythroblasts and leucocyte subgroups are counted, respectively, after erythrocytes and platelets are lysed by a hemolytic agent; in most of these methods, erythroblasts, lymphocytes and basophils could not be counted simultaneously.

CN Patent No. 1084473C discloses a method for four part differentiation of leucocytes, wherein a blood sample is treated by a reagent comprising a cationic surfactant, a non-ionic surfactant and an organic compound bearing an anionic group, and then lymphocytes are separated from other leucocytes by analyzing information of forward low-angle scattered light and forward high-angle scattered light. Because erythroblasts cannot be differentiated from lymphocytes by the scattered light method, they may interfere with differentiating and counting of lymphocytes when a blood sample including erythroblasts is treated by the above reagent. This may erroneously increase the counting of lymphocytes and leucocytes.

U.S. Pat. No. 5,155,044 discloses a reagent for analyzing leucocytes, which includes a lysis reagent and a termination reagent. The former is an acid hypoosmotic solution, which can quickly lyse erythrocytes and platelets, while the later is an alkaline saline solution, which can prevent the lysis reagent from further reacting with leucocytes by changing the action solution's pH and osmotic pressure, so as to keep the normal morphology of leucocytes. Then, DC signals and scattered light signals are detected. According to the above signal's comprehensive difference, leucocytes are differentiated into five groups. This method is simple and fast but is difficult to detect erythroblasts.

U.S. Pat. Nos. 5,538,893, 5,677,183 and 5,518,928 disclose a reagent and method for analyzing basophils. Reagents disclosed in these patents can render the nuclei of the leukocytes other than basophils naked and maintain the intactness of basophils alone. The impedance of or the low-angle scattered light from the cells is detected to obtain signals representing cell size. The side scattered light or high-angle scattered light from the cells is detected to obtain signals representing intracellular structure. By combining these two kinds of signals, the differentiating and counting of basophils are achieved. This method has some deficiency. For example, immature cells or heteromorphic lymphocytes in a blood sample may be incorrectly reported as basophils, resulting in erroneously increasing counts of basophils. Moreover, lipochondrion in some blood samples also may interfere with correct counting of leucocytes and basophils in these methods.

U.S. Pat. No. 5,298,426 discloses a reagent and method for counting erythroblasts. This patent discloses a method for detecting erythroblasts and leucocytes in two steps. There are two reagents: R1 and R2. R1 is an acid hypoosmotic solution containing one or more dyes, which can lyse erythrocytes and platelets, meanwhile, the dyes combine specifically to relative cells. For example, PI combines erythroblasts, Astrazon Yellow 3G combines eosinophils, and Acridine Red combines leucocytes. R2 is an alkaline saline solution, which can adjust pH and osmotic pressure of R1 to maintain normal morphology of leucocytes. Erythroblasts can be differentiated from leucocytes according to the difference of scattered light signals and fluorescence signals. This method can differentiate erythroblasts but it has some deficiency. Leucocytes are partly damaged when they are treated by R1, so the dye combining erythroblasts not only combines erythroblasts but also may combine leucocytes. This may affect accuracy of erythroblast counting. Moreover, this method needs two steps to get a final result, so the test time is longer and slows down test speed of the whole analyzer. At the same time, this method needs more kinds of dyes.

U.S. Pat. No. 6,664,110 B1 discloses a reagent and method for analyzing erythroblasts. The reagent is composed of components for lysing erythrocytes and dyes. In the reaction between the reagent and a blood sample, erythrocytes release hemoglobin to become an "erythrocyte ghost", and the fluorescent dyes combine cell nuclei including the nuclei of erythroblasts and leucocytes simultaneously. Scattered light signals and fluorescence signals are detected. Erythroblasts are differentiated from leucocytes according to comprehensive differences of these two kinds of signals.

U.S. Pat. No. 5,559,037 discloses a reagent and method for analyzing erythroblasts. The reagent disclosed in this patent comprises a component for lysing erythrocytes and a component for protecting leucocytes. The dye, such as PI, combines naked nuclei of erythroblasts. The component for protecting leucocytes protects leucocytes from being damaged and prevents the dye from staining leucocytes. Then, erythroblasts and leucocytes are differentiated according to ALL signals of 0° to 1°, LAS signals of 1° to 3° and fluorescence signals. This method also has some deficiency. The reagent just damages the membrane of erythroblasts and does not damage that of leucocytes so that dyes only enter inside of erythroblasts and combines with the nuclei of erythroblasts. However, a certain extent of damage of membrane of leucocytes may happen with the extension of storage time of a blood sample, which may result in dye entering inside of leucocytes and make it hard to differentiate and count erythroblasts accurately.

U.S. Pat. No. 5,874,310 discloses a reagent and method for analyzing erythroblasts. The reagent does not contain fluorescent dyes or nuclear dyes. In this method, erythrocytes are lysed by a hemolytic agent, and then impedance signals and scattered light signals are detected. Erythroblasts are differentiated from leucocytes according to the difference of these signals. Because erythroblasts have little difference from lymphocytes in cell size and morphology, the accuracy of counting erythroblasts by this method is not satisfying. Furthermore, the differentiating and counting of basophils is not reported by this method.

From the above description, most prior methods for differentiating and counting leucocytes cannot differentiate and count erythroblasts; whereas, most prior methods for differentiating and counting erythroblasts cannot differentiate and count leucocytes.

Therefore, it is beneficial to develop a reagent and method for differentiating and counting erythroblasts and leucocytes simultaneously. It will simplify the design of an analyzer and reagent, and it can increase the accuracy of counting lymphocytes and leucocytes. Because erythroblasts are similar to lymphocytes in cell size and morphology, they often interfere differentiating and counting of lymphocytes in many methods.

In one aspect of the present disclosure there is provided a compound having the general formula I:

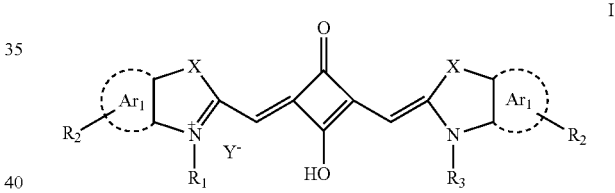

wherein
$Ar_1$ is an aromatic ring;
X is selected from at least one of the following: —O—, —S—, —Se— and

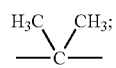

$R_1$ and $R_3$ are independently selected from $O_{3-20}$ alkenyl or $C_{3-20}$ alkynyl;
$R_2$ is selected from at least one of the following: hydrogen, carboxy, sulphonyl, $C_{1-20}$ saturated or unsaturated alkyl or alkoxyl.
$Y^-$ is an anion.

In another aspect of the present disclosure there is provided a conjugate comprising the above-said compound having the general formula I.

In yet another aspect of the present disclosure there is provided a composition, said composition comprising (i) the above-said compound having the general formula I or the conjugate thereof, and (ii) at least one surfactant selected from cationic surfactants and nonionic surfactants.

In another aspect of the present disclosure there is provided a method of preparing the composition disclosed in the present disclosure, said method comprises dissolving components of the composition disclosed in the present disclosure into water to prepare a composition comprising a single constituent; or dissolving the compound having the general formula I or the conjugate thereof into organic solvent and dissolving other components of the composition disclosed in the present disclosure into water to prepare a composition comprising two or more constituents.

In yet another aspect of the present disclosure there is provided a reagent kit for identifying erythroblasts and simultaneously differentiating and counting leucocytes, said reagent kit comprises a composition disclosed in the present disclosure, said composition can either be a composition comprising a single constituent or a composition comprising two or more constituents.

In yet another aspect of the present disclosure there is provided a method for identifying erythroblasts and simultaneously differentiating and counting leucocytes using a composition disclosed in the present disclosure.

According to the present disclosure, differentiating and counting of basophils, lymphocytes and erythroblasts may be achieved simultaneously using a single reagent and a single detection channel. In the present disclosure, not only basophils can be counted accurately but also lymphocytes and leucocytes can be counted accurately by decreasing erythroblasts' interference to lymphocytes and leucocytes. According to the present disclosure, erythroblasts, basophils, lymphocytes or leucocytes also can be differentiated and counted separately.

According to the present disclosure, lipochondrion in a blood sample may not interfere with differentiating and counting erythroblasts, basophils or leucocytes.

According to the present disclosure, the lower concentration of dye may also achieve satisfactory differentiation effect.

These and other features of the present disclosure will become apparent by reference to the following drawings and specific embodiments of the present disclosure.

Definitions

Unless otherwise specified, the terms as used herein have the following meanings.

The term "aromatic ring" as used herein refers to single ring or multi-link aromatic ring having 3-20 carbon atoms, optionally further comprising 1-3 hetero atoms selected from N, O and S, such as an aromatic ring having at least six-member carboatomic ring or alternatively benzene ring or naphthalene ring.

The term "alkyl" as used herein individually or in combination with other groups refers to straight or branched alkyl groups containing 1-18 carbon atoms, such as 1-12, or alternatively 1-8, or 1-6 carbon atoms. Reference to a single straight alkyl such as "n-propyl" specifically means a straight alkyl group, while reference to a single branched alkyl such as "isopropyl" specifically means a branched alkyl group. For example, "$C_{1-6}$alkyl" includes $C_{1-4}$alkyl, $C_{1-3}$alkyl, methyl, ethyl, n-propyl, isopropyl and tert-butyl. The same rules apply to other groups as used throughout the present specification.

The term "alkoxyl" refers to "alkyl" as defined above containing an oxygen atom; said group combines the rest of the parent molecule by the oxygen atom.

The term "alkenyl" as used herein refers to a straight or branched carbon chain containing 2-30 carbon atoms, such as 6-14, or alternatively 2-4 carbon atoms, and there is one or more unsaturated double bonds in the molecular chain.

The term "alkynyl" as used herein refers to a straight or branched carbon chain containing 2-30 carbon atoms, such as 6-14, or alternatively 2-4 carbon atoms, and there is one or more unsaturated triple bonds in the molecular chain.

The term "halogen" as used herein includes fluorine, chlorine, bromine and iodine.

The term "sulphonyl" as used herein refers to the —$SO_3H$ group or the —$SO_3^-M$ group, wherein M is a counterion including such ions as alkali metal ions (e.g., $K^+$ ion) or alkaline earth metal ions.

The term "biological sample" as used herein includes but is not limited to peptide, protein, nucleic acids and cellular nucleic acids in blood (including DNA, RNA, and organelles containing DNA and RNA).

Compounds According to the Present Disclosure

In one aspect of the present disclosure there is provided a fluorescent dye which can combine with nucleic acids in blood (including DNA, RNA, and organelles containing DNA and RNA). Said fluorescent dye can emit fluorescence after they are excited by a predetermined wavelength exciting light. A fluorescent dye which may be used in the present disclosure is a compound having the general formula I;

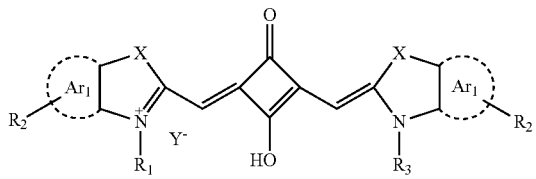

Formula I wherein $Ar_1$ is an aromatic ring;

X is selected from at least one of the following: —O—, —S—, and

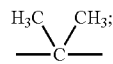

$R_1$ and $R_3$ are independently selected from $C_{3-20}$ alkenyl or $C_{3-20}$ alkynyl;

$R_2$ is selected from at least one of the following: hydrogen, carboxy, sulphonyl, $C_{1-20}$ saturated or unsaturated alkyl or alkoxyl.

$Y^-$ is an anion.

In one embodiment, $Ar_1$ is aromatic ring having at least a six-member carboatomic ring, or alternatively a benzene ring or a naphthalene ring.

In one embodiment, X is selected from —S—, or

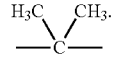

In one embodiment, $R_1$ is selected from $O_{3-18}$ alkenyl or $C_{3-18}$ alkynyl, or alternatively $C_{3-8}$ alkenyl or $C_{3-8}$ alkynyl.

In one embodiment, $R_3$ is selected from $C_{3-18}$ alkenyl or $C_{3-18}$ alkynyl, or alternatively $C_{3-8}$ alkenyl or $C_{3-8}$ alkynyl.

In one embodiment, $R_2$ is selected from hydrogen, carboxy, sulphonyl, $C_{1-12}$ saturated or unsaturated alkyl or alkoxyl. In another embodiment, $R_2$ is selected from hydrogen, carboxy, sulphonyl, $C_{1-8}$ saturated or unsaturated alkyl or alkoxyl.

In one embodiment, Y⁻ is selected from at least one of the following: $Cl^-$, $Br^-$, $I^-$, $ClO_4^-$, $PF_6^-$ and $p\text{-}CH_3C_6H_4\text{—}SO_3^-$.

In one embodiment, the compound of formula I is selected from Compound 1, Compound 2, Compound 3, Compound 4, Compound 5, Compound 6, Compound 7, Compound 8, Compound 9, Compound 10, Compound 11, Compound 12, Compound 13, Compound 14, Compound 15, Compound 16, Compound 17, Compound 18, Compound 19, Compound 20, Compound 21, Compound 22, or Compound 23, wherein such compounds have the following structures:

Compound 1

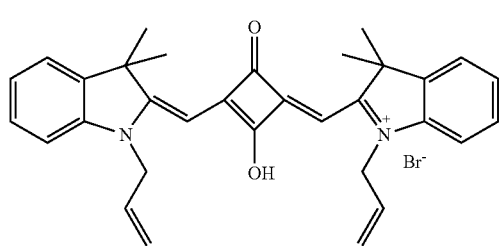

Compound 2

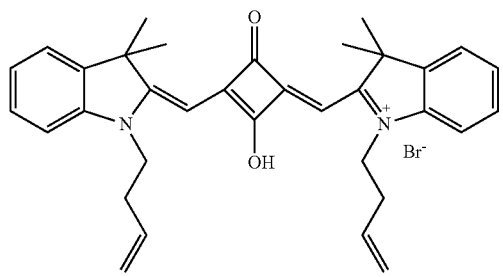

Compound 3

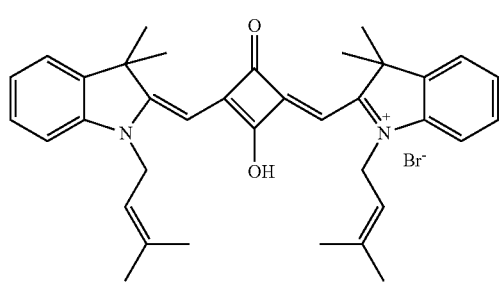

Compound 4

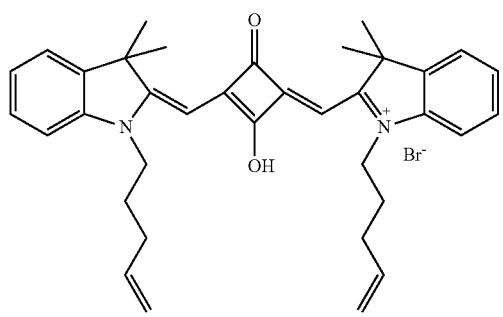

Compound 5

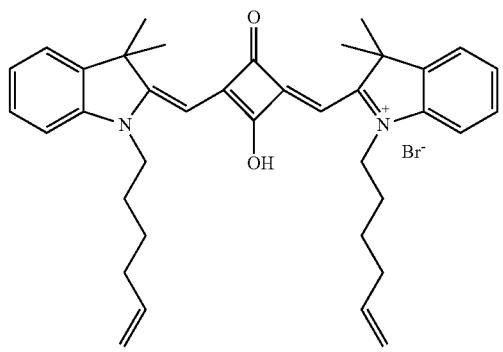

Compound 6

Compound 7

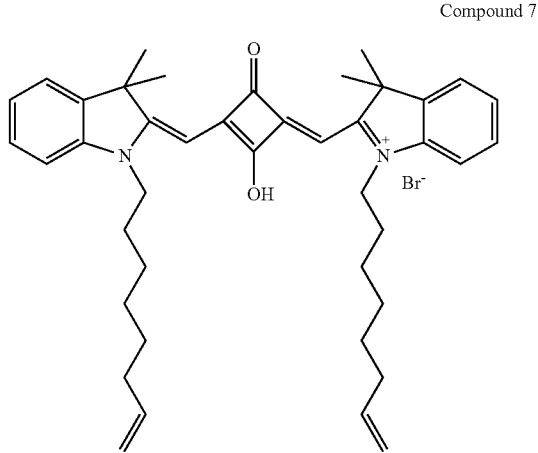

Compound 8

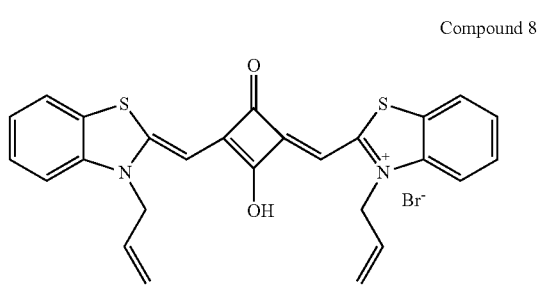

Compound 9
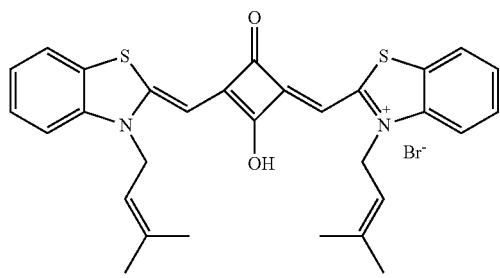
Compound 10
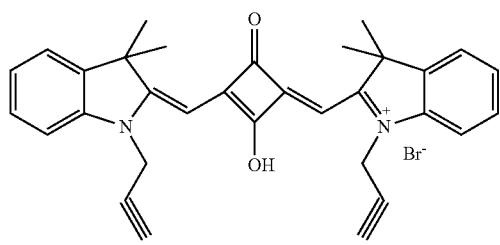
Compound 11
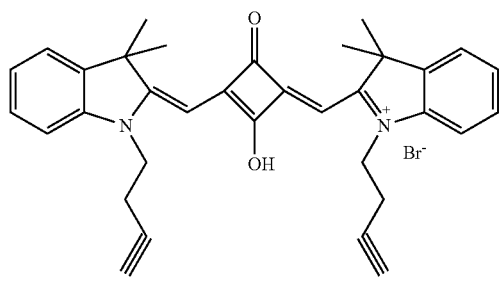
Compound 12
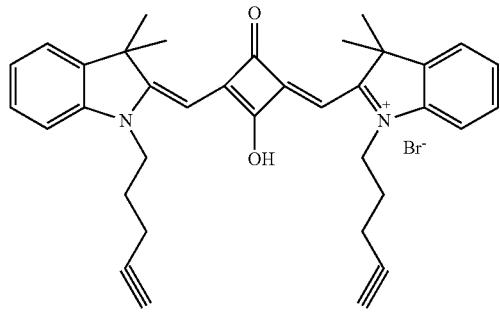
Compound 13
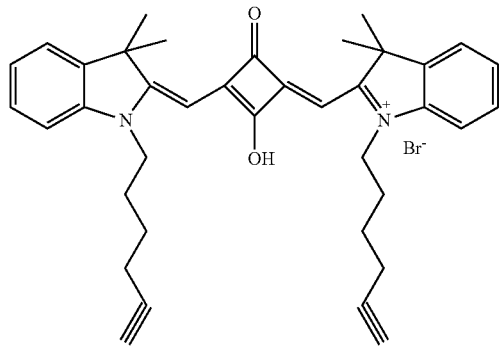
Compound 14
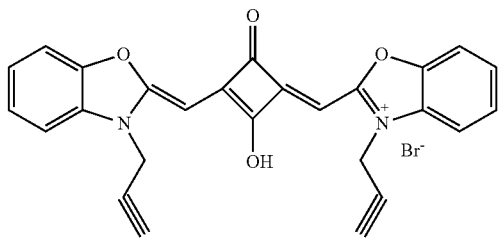
Compound 15
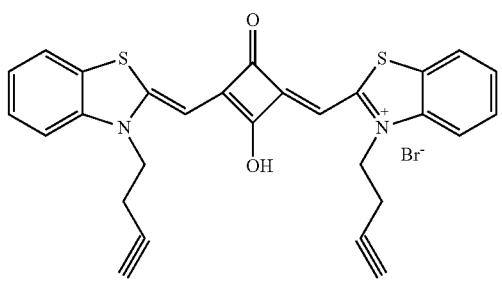
Compound 16
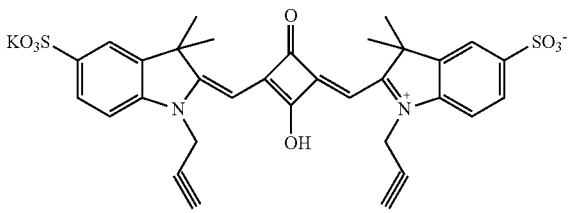
Compound 17
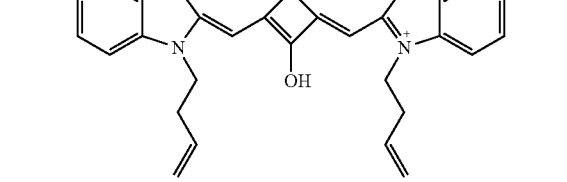
Compound 18
Compound 19
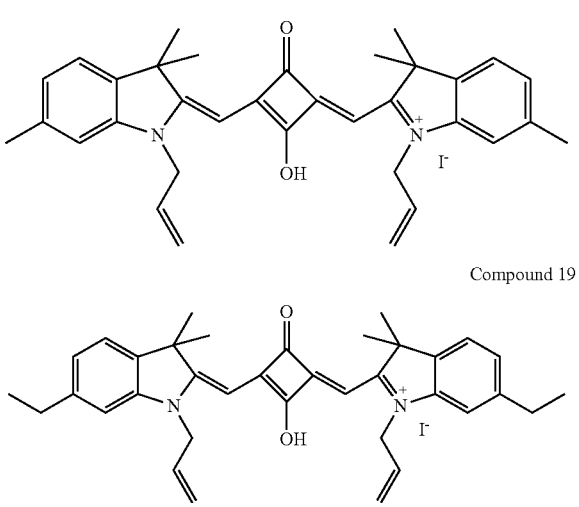

Compound 20

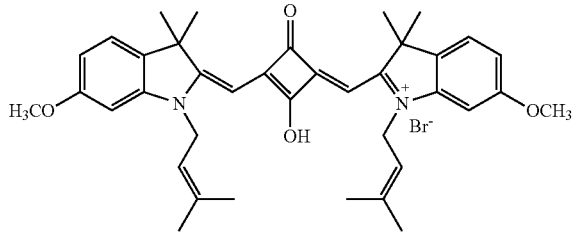

Compound 21

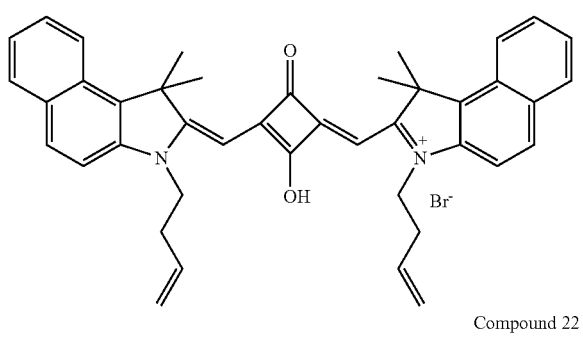

Compound 22

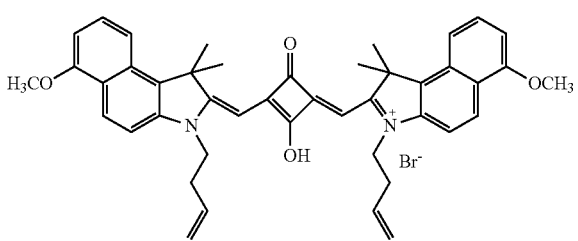

Compound 23

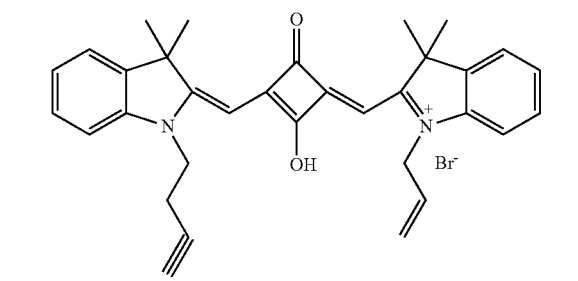

In some embodiments, the compound according to the present disclosure can be directly used for staining biological samples in the form of salts as described herein. Alternatively, in one embodiment, the compound according to the present disclosure in some examples can be used in the form of derivatives of the compound having the general formula I, said derivatives including, but not limited to, conjugates.

The compounds according to the present disclosure emit little or no fluorescence when they unbind to nucleic acids, but have a rapidly increased fluorescence intensity upon binding to nucleic acids to form a complex with the light spectrum located in the near-infrared region so that interference from background fluorescence can be avoided and accuracy of test can be improved. Then, many types of biological samples can be stained in flow cytometry.

Typically, conjugates are used in the fluorescence activated cell sorter (FACS). "Conjugate" as used herein refers to the compound formed by attaching the compound according to the present disclosure to other molecules via covalent bonds.

Molecules that can be conjugated with the compound according to the present disclosure may be those that specifically bind to cells or cell components, including, but not limited to, antibodies, antigens, receptors, ligands, enzymes, substrates, coenzymes or the like. Generally, the sample to be detected is incubated with a conjugate for a period of time so that the conjugate binds specifically to certain cells or cell components in the sample to be detected. The binding of the conjugate to the cells or cell components can also be referred to as staining. The above staining steps can be repeated in sequence for several times, or a variety of conjugates can be used for concurrent multistaining. At the completion of staining, the sample is analyzed in the fluorescence activated cell sorter wherein the excitation light source excites the compound according to the present disclosure in the conjugate and the detection apparatus detects the emitted light generated by the excited compound.

Alternatively, in another embodiment, the conjugates can also be used in solid phase immunological assays, e.g. sandwich immunological assays. The techniques of solid phase immunological assays are well-known in the art and can be found in standard textbooks. Said conjugates can be used as various suitable components in solid phase immunological assays.

Process for Preparing the Compound

The compounds according to the present disclosure can be synthetically obtained using the general methods well known in the art. In particular, some of the intermediates of the compounds according to the present disclosure can be synthetically obtained by the following process.

The unsubstituted or substituted compound of the formula IV is used as the raw material to react with the halide of the formula $R_1X$ or $R_3X$ (X is F, Cl, Br or I):

Formula IV

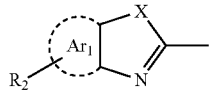

to obtain the quaternary ammonium salt intermediate of the formula V or formula VI:

Formula V

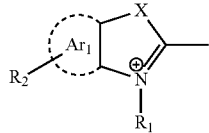

Formula VI

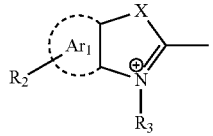

wherein $R_1$, $R_2$, $R_3$, X, $Ar_1$ ring are respectively as defined above for the compound having the general formula I.

For example, the following reactions yield the corresponding quaternary ammonium salt intermediates.

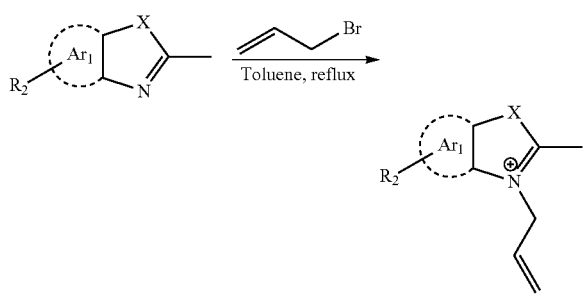

Then, the thus obtained quaternary ammonium salt intermediate is condensed with a linker molecule such as squaric acid to obtain the compound having the general formula I:

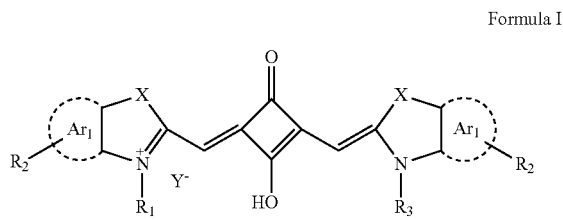

Formula I wherein X, Y, $R_1$, $R_2$, $R_3$, and $Ar_1$ ring are respectively as defined above.

The resulting compounds can be recovered using the separation and purification techniques well known in the art to achieve the desired purity.

The raw materials used in the present disclosure are commercially available, or can be readily prepared from raw materials known in the art using methods known to those skilled in the art or methods disclosed in the prior art.

A compound having the general formula I can be used in a concentration between 0.05 ppm and 200 ppm. In one embodiment, the range is 0.1 ppm to 20 ppm. In another embodiment, the range is 0.5 ppm to 10 ppm. Exemplary compounds according to the present disclosure have a higher fluorescence quantum yield, so that its usage amount may be reduced in reagent preparation, where less compound can achieve a similar differentiation effect.

The Composition of the Present Disclosure

In one embodiment according to the present disclosure, a composition for staining biological samples is further provided, which comprises (i) the above-said compound having the general formula I or the conjugate thereof, and (ii) at least one surfactant selected from a cationic surfactant or a nonionic surfactant.

Cationic Surfactants

The cationic surfactants useful in the present disclosure may be quaternary ammonium salt-type cationic surfactants having the following general formula II:

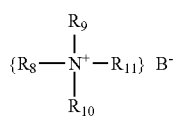

Formula II wherein
$R_8$ is alkyl or alkenyl having 6 to 14 carbon atoms;
$R_9$ and $R_{10}$ are independently selected from $C_{1-4}$ alkyl or $C_{2-4}$ alkenyl;
$R_{11}$ is selected from $C_{1-4}$ alkyl, $C_{2-4}$ alkenyl or benzyl; and
B is a halide ion.

In one embodiment, $R_8$ is selected from at least one of the following: hexyl, octyl, decyl, dodecyl and myristyl group. In another embodiment, $R_8$ is selected from decyl, dodecyl or myristyl group.

In one embodiment, $R_9$ and $R_{10}$ are independently selected from at least one of following: methyl, ethyl, propyl, butyl and butenyl group. In another embodiment $R_9$ and $R_{10}$ are independently selected from methyl, ethyl or propyl.

Nonionic Surfactants

The nonionic surfactants useful in the present disclosure may be a polyoxyethylene-type nonionic surfactant having the general formula III:

$$R_A\text{-}R_B\text{—}(CH_2CH_2O)_n\text{—}H \qquad \text{Formula III}$$

wherein
$R_A$ is alkyl or alkenyl having 8 to 23 carbon atoms, such as in one embodiment straight alkyl including octyl, decyl, lauryl, tetradecyl, cetyl, and stearyl, or in another embodiment straight alkyl including lauryl, tetradecyl and cetyl;
$R_B$ is selected from —O—,

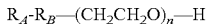

or —COO—; and
n is an integer of between 8-30.

In one embodiment, said nonionic surfactant is selected from at least one of the following: octylphenylpolyoxyethylene ether, polyoxyethylene(10)cetyl ether, polyoxyethylene(23)cetyl ether, polyoxyethylene(25)cetyl ether and polyoxyethylene(30)cetyl ether and the like In another embodiment, the nonionic surfactant is polyoxyethylene(30)cetyl ether.

The hemolytic activity of the surfactant is in proportion to the chain length of their side chain ($R_8$ of the cationic surfactants of formula II, $R_A$ of the nonionic surfactants of formula III). Generally speaking, the longer the side chain, the higher hemolytic activity they have, and the lower working concentration is required. So, the working concentration of surfactants varies with different kinds of surfactants. In principle, any concentration can be used as long as the hemolytic activity is capable of resulting in lysing erythrocytes, making the cell nuclei of erythroblasts naked, and partly damaging the membrane of leucocytes so as to let fluorescent dyes enter inside of cells for binding nucleic acid material.

Said cationic surfactant can be used in a concentration between 10 mg/L and 10000 mg/L. In one embodiment, the range is between 150 mg/L to 1500 mg/L.

Said octylphenylpolyoxyethylene ether can be used in a concentration between 20 mg/L and 10000 mg/L, particularly between 100 mg/L to 5000 mg/L. Said polyoxyethylene(10) cetyl ether can be used in a concentration between 10 mg/L and 10000 mg/L, particularly between 50 mg/L to 4000 mg/L. Said polyoxyethylene(23)cetyl ether can be used in a concentration between 8 mg/L and 8000 mg/L, particularly between 20 mg/L to 2000 mg/L. Said polyoxyethylene(25) cetyl ether can be used in a concentration between 5 mg/L and 5000 mg/L, particularly between 10 mg/L to 1000 mg/L. Said polyoxyethylene(30)cetyl ether can be used in a concentration between 10 mg/L and 2000 mg/L, particularly between 5 mg/L to 500 mg/L.

Organic Compound Bearing an Anionic Group

Compositions disclosed in the present disclosure may optionally comprise an organic compound bearing an anionic group. Although not hoping to be bound by any theory, an organic compound bearing an anionic group mainly speeds up lysis of erythrocytes, shortens the hemolytic time, and improves the differentiation effect. Adding an organic compound bearing an anionic group will speed up lysis of erythrocytes, not fully lysed erythrocytes nearly all become erythrocyte ghosts, so that erythrocytes' interference to NRBC analysis will be reduced. On the other hand, it is known from experiments that an organic compound bearing an anionic group may make NRBC group more congregated in a scattergram and conduce to differentiating and counting of basophils.

In one embodiment, said organic compound bearing an anionic group may be selected from salicylic acid and salts thereof or benzoic acid and salts thereof.

Said organic compound bearing an anionic group can be used in a concentration that makes hemolytic time as short as possible on the promise that cells can be differentiated markedly. The usual range of concentration is 10 mg/L to 50000 mg/L, such as 500 mg/L to 5000 mg/L.

Other Components

A composition disclosed in the present disclosure may optionally comprise a buffering agent, an osmotic regulating agent, a preservative or a metallo-chelate.

Buffering Agent

A composition disclosed in the present disclosure may optionally comprise a buffering agent for adjusting the pH. The lower the pH value, the stronger the hemolytic activity of the composition. However, it is impossible to differentiate basophils from other leucocytes in a condition of very low pH, and it is hard to differentiate erythroblasts from leucocytes in a condition of very high pH. Therefore, it is better that the pH of compositions according to the present disclosure is maintained in a certain range, such as 2-6, or alternatively 2.5-4.5.

Buffering agents which may be used in the composition of the present disclosure are citric acid, formic acid, acetic acid, glycine, phthalic acid, tartaric acid, malic acid, and maleic acid, etc. They are generally used in a concentration of 0.1-1000 mmol/L, for example 1-100 mmol/L.

Osmotic Regulating Agent

A composition disclosed in the present disclosure may optionally comprise an osmotic regulating agent, such as alkali metal salts and carbohydrates.

Although not hoping to be bound by any theory, in general, the lower osmotic pressure the better hemolysis effect. However, in a condition of very low osmotic pressure, membranes of leucocytes may be damaged excessively. Therefore, the osmotic pressure of the compositions according to the present disclosure may be maintained in a range of 20-150 mOsm/kg.

Preservative and Metallo-Chelate

A composition disclosed in the present disclosure may optionally comprise a conventional preservative or metallo-chelate to extend their shelf-life.

In one embodiment, the preservative is Kathon and methylparaben. They can be used in the concentration of 0.05-1.5 g/L, such as 0.05 g/L-0.5 g/L.

There is no particular limitation on the concentration of said metallo-chelate. A suitable range of concentration is 0.05 g/L-1 g/L.

Preparation Method for Composition According to the Present Disclosure

In one aspect of the present disclosure there is provided a preparation method for above compositions. In one exemplary method, all components of the composition according to the present disclosure are dissolved into water to prepare a composition comprising a single constituent. In another exemplary method, the compound having the general formula I is dissolved into organic solvent and the other components are dissolved into water to prepare a composition comprising two or more constituents. There are no particular limitations on the identity of organic solvents, so long as they can fully dissolve the compound having the general formula I and are somewhat soluble in water, and the common organic solvents such as methanol, ethanol, glycol, glycerol and dimethylsulfoxide can be used.

Reagent Kit According to the Present Disclosure

In one aspect of the present disclosure there is provided a reagent kit. Said kit comprises a composition according to the present disclosure. Said kit can be used to treat a blood sample. For example, the kit can be used to treat a blood sample containing erythroblasts and identify erythroblasts and simultaneously differentiate and count leucocytes.

In said kit, components of the composition according to the present disclosure can be packed in single package, or the fluorescent dye having the general formula I and other components are packed separately to form two or more packages.

Because fluorescent dyes of the composition according to the present disclosure are typically more stable in a non-aqueous solvent, it may be better to be stored separately from the water soluble component of the reagent disclosed in the present disclosure. In one embodiment, said fluorescent dyes are stored in organic solvent. There are no particular limitations on the variety of organic solvents, so long as they can fully dissolve said fluorescent dyes and are somewhat soluble in water. Common organic solvents such as methanol, ethanol, glycol, glycerol and dimethylsulfoxide can be used.

Said fluorescent dyes can be stored in the organic solvent in any concentration, as long as the dye can be fully dissolved and the concentration is not lower than its final working concentration. Usually, the range of the storage concentration of the fluorescent dye may be 0.01 ppm to 1000 ppm, or alternatively, 1 ppm to 100 ppm.

In the present disclosure, said water soluble component is also referred to as "hemolytic agent" and the component comprising said fluorescent dye referred to as "dyeing liquid". When a reagent kit disclosed in the present disclosure is used, the dyeing liquid and the hemolytic agent can either be mixed with a blood sample in a certain volume ratio for a period of time prior to conducting detection, or be mixed with each other and then mixed with a blood sample in a certain volume ratio prior to conducting detection. The volume ratio of said dyeing liquid to said hemolytic agent is not particularly limited, and they are generally mixed in a volume ratio of 1:10 to 1:100, such as 1:40 to 1:60.

In another aspect of the present disclosure there is provided a process for preparing a reagent kit, wherein the process comprises:

(i) dissolving an amount of each component of the present reagent into water, adjusting the pH of the solution and diluting to a certain volume, and packaging it in the kit in the form of a single package; or (ii) dissolving an amount of compound having the general formula I of the present reagent into an organic solvent, diluting to a certain volume and packaging; dissolving an amount of each of the other components of the present reagent into water, adjusting the pH of the solution and diluting to a certain volume, and packaging the two separate packages in the form of a kit.

Said other components refer to the water soluble components in the present reagent other than compound having the general formula I. Other components can either be (1) dissolved into water together, adjusted the pH and diluted to a certain volume, and packed in the kit in the form of a single package, or (2) be dissolved with each of the other components into water separately, adjusted the pH and diluted to a certain volume, and packed them in the kit in the form of multiple packages.

As mentioned above, compounds having the general formula I used in the present reagent are typically more stable in non-aqueous solvents. Thus, it may be desirable to store the compound separately from the water soluble components of the composition of the present disclosure. For example, it may be desirable to store the compound having the general formula I in an organic solvent, and then pack the compound having the general formula I in the kit separately from the other components.

Usage of the Composition According to the Present Disclosure

In another aspect of the present disclosure there is provided a method for identifying erythroblasts and simultaneously differentiating and counting leucocytes, said method comprising the following steps of:

(a) mixing a blood sample with the composition according to the present disclosure to form a cell suspension, where the fluorescent dyes enter inside of cells and combine with nucleic acids;

(b) detecting scattered light signals and fluorescence signals from cells in the cell suspension: the stained cells can emit fluorescence signals with different strength according to the different degree of combination after they are excited by an exciting light with a predetermined wavelength. Different types of cells have different sizes, and may have different changes in size after reacting with the above compositions, so that they will emit a scattered light with different strength; and (c) differentiating erythroblasts and leucocytes in terms of the difference of the scattered light signals and fluorescence signals, and reporting the counting result of different type of cells.

When mixing the compositions according to the present disclosure with a blood sample, components of the composition can be mixed with each other and then mixed with a blood sample, or mixed with a blood sample at the same time. The mixture is incubated for a period of time at a certain temperature to lyse erythrocytes and platelets, to make the nucleus of erythroblasts naked, and to partly damage leucocytes to form some small pores in the membrane to facilitate staining. There is no special requirement regarding the ratio between the blood sample and the composition of the present disclosure, as long as the ratio is such that different types of cells can be satisfactorily distinguished. In one embodiment, the ratio between the blood sample and the composition is 1:10~1:500. Leucocytes are partly damaged by the composition so that the compound having the general formula I used herein as fluorescent dye may enter inside of cells and combine nucleic acids. Said nucleic acids refer to DNA, RNA in cell nucleus and organelles containing DNA and RNA.

The above-mentioned scattered light may include 1°-10° scattered light which reflexes the information about cell size, or 90° scattered light which reflexes complicity degree of intracellular structure. The above-mentioned fluorescence may include red fluorescence in which stained cells emit after they are excited by an exciting light with a predetermined wavelength, wherein the exciting light is emitted from a semiconductor laser and the wavelength is about 635 nm.

When a blood sample is treated according to one embodiment of the present disclosure, erythrocytes are fully lysed and some not fully lysed erythrocytes become "erythrocyte ghosts" so as to bring little interference to subsequent detection of scattered light signals and fluorescent light signals. Meanwhile, nuclei of erythroblasts are naked to combine a fluorescent dye directly. The naked nuclei of erythroblasts which are formed after treatment by the composition generate pycnosis so that the combining amount of fluorescence dye decreases to make fluorescence signals weaker. Moreover, erythroblasts are a naked nucleus structure after treatment so that 1°-10° scattered light signal from them is weak. Therefore, erythroblasts can be differentiated from leucocytes.

Leucocytes comprise several subgroups such as basophiles and lymphocytes. The cell characters of subgroups are different from each other. The extent of cell membrane damage is different after cells are treated by the composition so that the amount of dye which enters inside of cells is different. And the nucleus size of subgroups is also different from each other. As a result, combining amounts of fluorescent dye to intracellular nucleic acids is different in various kinds of leucocytes, so that various kinds of leucocytes have different fluorescence signals. Because lymphocytes have the smallest size among various subgroups of leucocytes, intracellular nucleic acids are relatively less, so lymphocytes can be differentiated from other leucocytes by using a suitable fluorescent dye.

Basophils have a certain acid resistance. In one embodiment of the present disclosure, the composition may damage the membrane of basophils less than that of other leucocytes which are similar to basophiles in cell size, so basophils may emit weaker fluorescence signals when stained by a suitable fluorescent dye. Moreover, basophils have relatively larger cell size. In terms of these two differences, basophils can be differentiated from other leucocytes such as eosinophils or neutrophils. In summary, the reagent and method according to the present disclosure can be used to identify erythroblasts, as well as differentiate leucocytes, such as differentiate lymphocytes and/or basophils from other leucocytes, and respectively count erythroblasts, basophils, lymphocytes and the total amount of leucocytes.

EXAMPLES

The present disclosure is further illustrated by the following particular examples to which or by which the present disclosure is not limited.

Unless otherwise stated, the chemicals used in the preparation of the reagents are analytically pure, wherein a compound having the general formula I used as a fluorescent dye may be dissolved into alcohol to prepare a stock solution. The detection apparatus used in the following examples for detecting blood cells is the BC series blood analyzer manufactured by Shenzhen Mindray Bio-Medical Electronics Co. Ltd (Shenzhen, People's Republic of China), with the detection wavelength being 635 nm. The schematic diagram of the blood analyzer is shownin FIG. 1.

Example 1

Synthesis of Compound 1

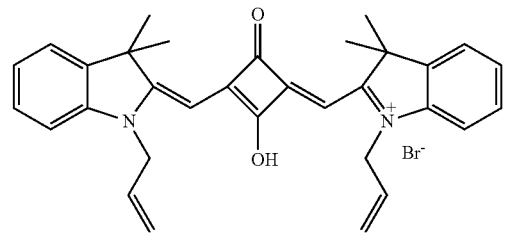

Compound 1

0.1 mol of 2,3,3-trimethylindole, 0.12 mol of 3-bromoprop-1-ene and 25 mL of acetonitrile which was used as a solvent were added into a 100 mL 3-neck flask equipped with a reflux condenser and a magnetic stirrer with heating. The mixture was reacted in darkness under reflux in an argon atmosphere for 24 hours. The reaction mixture was evaporated under reduced pressure to remove some solvent and then some petroleum ether was added. The crude product was precipitated out by ultrasonic vibration, which was brown-reddish oil and was directly used in next step of reaction.

0.01 mol of the brown-reddish product, 0.005 mol of squaric acid, and 8 mL of benzene, 6 mL of n-butanol and 6 mL of pyridine which were used as solvents were added together into a 50 mL 3-neck flask, and the mixture was stirred and heated to reflux under argon for 6 hours. Then the reaction was stopped and cooled to room temperature. The product was precipitated out by adding an excess amount of ethyl ether, filtered, washed with a suitable amount of ethyl ether, and dried to obtain a dark blue solid. The dark blue solid was purified by silica gel column chromatography eluting with a gradient of dichloromethane:methanol=100:0→100:12. The blue fractions were collected and the solvents therein were removed by rotary evaporation. The resulting residue was dried in a vacuum drying chamber at 45° C. for 24 hours to afford the title compound as a blue solid having a golden metallic luster, with a yield of 43%.

MS (EI) $C_{32}H_{33}BrN_2O_2$ m/z: 477.6 $[M-Br]^+$.

Example 2

Synthesis of Compound 2

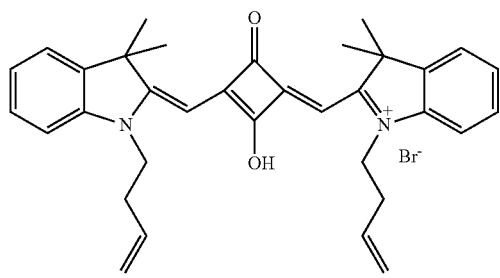

Compound 2

Under argon, 0.1 mol of 2,3,3-trimethylindole, 0.12 mol of 4-bromobut-1-ene were dissolved in 25 mL toluene. The mixture was reacted in darkness under reflux for 24 hours. The reaction mixture was evaporated under reduced pressure to remove some solvent and some petroleum ether was added. The crude product was precipitated out by ultrasonic vibration, which was brown-reddish block-like mass and was directly used in next step of reaction.

0.01 mol of the brown-reddish product, 0.005 mol of squaric acid, and 8 mL of toluene, 6 mL of n-butanol and 6 mL of pyridine which were used as solvents were added together into a 50 mL 3-neck flask, and the mixture was stirred under reflux in an argon atmosphere for 7 hours. Then the reaction was cooled to room temperature. The product was precipitated out by adding an excess amount of ethyl ether, filtered, washed with some ethyl ether, and dried to obtain a dark blue solid. The dark blue solid was purified by silica gel column chromatography eluting with a gradient of dichloromethane:methanol=100:0→100:12. The blue fractions were collected and the solvents therein were removed by rotary evaporation. The resulting residue was dried in a vacuum drying chamber at 45° C. for 24 hours to afford the title compound as a blue solid having a golden metallic luster, with a yield of 45%.

MS (EI) $C_{34}H_{37}BrN_2O_2$ m/z: 505.7 $[M-Br]^+$.

Example 3

Synthesis of Compound 3

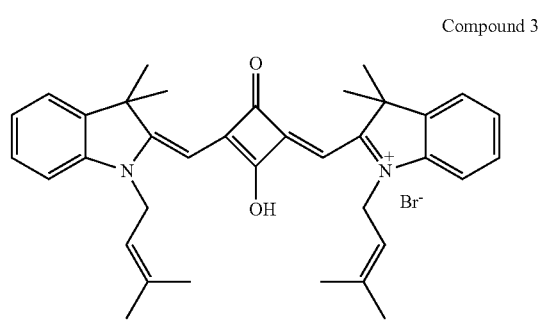

Compound 3

0.08 mol of 2,3,3-trimethylindole, 0.12 mol of 1-bromo-3-methylbut-2-ene and 10 mL of toluene which was used as a solvent were added into a 250 mL 3-neck flask equipped with a reflux condenser and a magnetic stirrer with heating. The mixture was reacted under reflux in an argon atmosphere for 12 hours. The reaction system was cooled to room temperature before a suitable amount of ethyl acetate was added therein. A crude product was precipitated out by ultrasonic vibration, which was triturated in ethyl acetate and then was washed by petroleum ether to obtain a dark brown-reddish block-like mass which was directly used in the next step of reaction.

0.08 mol of the brown-reddish product, 0.04 mol of squaric acid, and 4 mL of toluene, 4 mL of n-butanol and 5 mL of pyridine which were used as solvents were added together into a 25 mL 3-neck flask, and the mixture was stirred and heated to reflux in an argon atmosphere for 10 hours. Then the reaction was stopped and cooled to room temperature. The product was precipitated out by adding an excess amount of ethyl ether, filtered, washed with a suitable amount of ethyl ether, and dried to obtain a dark blue solid. The dark blue solid was purified by silica gel column chromatography eluting with a gradient of dichloromethane:methanol=100:0→100:15. The blue fractions were collected and the solvents therein were removed by rotary evaporation. The resulting residue was dried in a vacuum drying chamber at 45° C. for 24 hours to afford the title compound as a blue solid having a golden metallic luster, with a yield of 23%.

MS (EI) $C_{36}H_{41}BrN_2O_2$ m/z: 533.7 $[M-Br]^+$.

Example 4

Synthesis of Compound 8

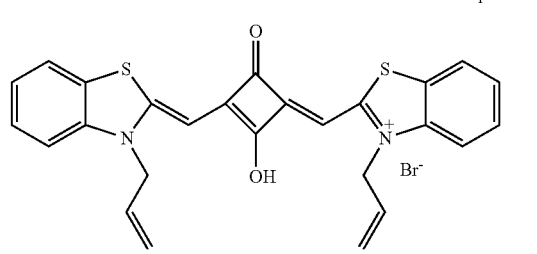

Compound 8

0.1 mol of 2-methylbenzothiazo, 0.25 mol of 3-bromoprop-1-ene and 25 mL of dimethyl benzene which was used as a solvent were added into a 100 mL 3-neck flask equipped with a reflux condenser and a magnetic stirrer with heating. The mixture was reacted under reflux in an argon atmosphere for 36 hours. The reaction system was cooled to room temperature before standing for 2 hours. The supernatant was discarded and the low-layer product was washed by a suitable amount of ethyl ether several times to obtained a gray block-like mass which was directly used in the next reaction.

0.08 mol of the gray product, 0.004 mol of squaric acid, and 6 mL of benzene, 4 mL of n-butanol and 4 mL of pyridine which were used as solvents were added together into a 50 mL 3-neck flask, and the mixture was stirred under reflux for 6 hours in an argon atmosphere. Then the reaction was cooled to room temperature. The product was precipitated out by adding an excess amount of ethyl ether, filtered, washed with a suitable amount of ethyl ether, and dried to obtain a dark blue-green solid. The dark blue-green solid was purified by silica gel column chromatography eluting with a gradient of dichloromethane:methanol=100:0→100:10. The blue fractions were collected and the solvents therein were removed by rotary evaporation. The resulting residue was dried in a vacuum drying chamber at 45° C. for 24 hours to afford the title compound as a blue-green solid having a golden metallic luster, with a yield of 37%.

MS (EI) $C_{26}H_{21}BrN_2O_2S_2$ m/z: 457.6 $[M-Br]^+$.

Example 5

Synthesis of Compound 10

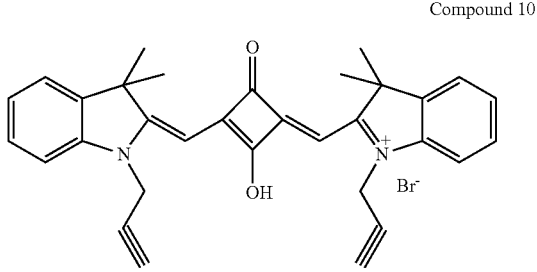

Compound 10

0.1 mol of 2,3,3-trimethylindole, 0.25 mol of 3-bromoprop-1-yne and 25 mL of toluene which was used as a solvent were added into a 100 mL 3-neck flask equipped with a reflux condenser and a magnetic stirrer with heating. The mixture was reacted under reflux in an argon atmosphere for 48 hours. The reaction system was cooled to room temperature before standing for 2 hours. The supernatant was discarded and the low-layer product was washed by a suitable amount of ethyl ether for several times to obtained a gray block-like mass which was directly used in the next step of reaction.

0.04 mol of the gray product, 0.02 mol of squaric acid, and 5 mL of toluene, 4 mL of n-butanol and 4 mL of pyridine which were used as solvents were added together into a 3-neck flask, and the mixture was stirred and heated to reflux under argon for 6 hours. Then the reaction was cooled to room temperature. The product was precipitated out by adding an excess amount of ethyl ether, filtered, washed with a suitable amount of ethyl ether, and dried to obtain a dark blue solid. The dark blue solid was purified by silica gel column chromatography eluting with a gradient of dichloromethane:methanol=100:0→100:20. The blue fractions were collected and the solvents therein were removed by rotary evaporation. The resulting residue was dried in a vacuum drying chamber at 45° C. for 24 hours to afford the title compound as a blue solid having a golden metallic luster, with a yield of 29%.

MS (EI) $C_{32}H_{29}BrN_2O_2$ m/z: 473.6 $[M-Br]^+$.

Example 6

Synthesis of Compound 11

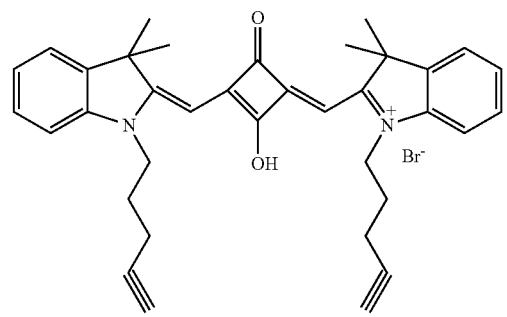

Compound 11

0.05 mol of 2,3,3-trimethylindole, 0.10 mol of 5-bromopent-1-yne and 10 mL of o-dichlorobenzene which was used as a solvent were added into a 250 mL 3-neck flask equipped with a reflux condenser and a magnetic stirrer with heating. The mixture was reacted under reflux in an argon atmosphere for 28 hours. The reaction system was cooled to room temperature before a suitable amount of ethyl acetate was added therein. A crude product was precipitated out by ultrasonic vibration, which was triturated in ethyl acetate and then was filtered to obtain a brown-reddish block-like mass which was directly used in the next step of reaction.

0.005 mol of the brown-reddish mass product, 0.0025 mol of squaric acid, and 4 mL of benzene, 3 mL of n-butanol and 3 mL of pyridine which were used as solvents were added together into a 50 mL 3-neck flask, and the mixture was stirred and heated to reflux in an argon atmosphere for 6 hours. Then the reaction was stopped and cooled to room temperature. The product was precipitated out by adding an excess amount of ethyl ether, filtered, washed with a suitable amount of ethyl ether, and dried to obtain a dark blue solid. The dark blue solid was purified by silica gel column chromatography eluting with a gradient of ethyl acetate:petroleum ether=100:0→100:20. The blue fractions were collected and the solvents therein were removed by rotary evaporation. The resulting residue was dried in a vacuum drying chamber at 45° C. for 24 hours to afford the title compound as a blue solid having a golden metallic luster, with a yield of 33%.

MS (EI) $C_{36}H_{37}BrN_2O_2$ m/z: 529.7 $[M-Br]^+$.

Example 7

Synthesis of Compound 23

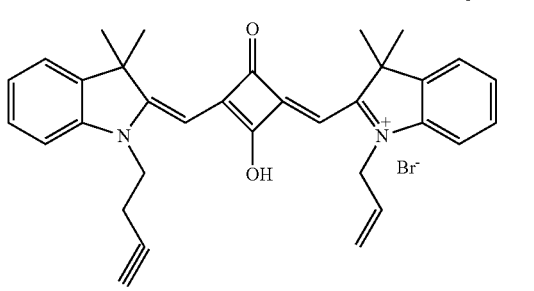

Compound 23

0.003 mol of squaric acid, 8 mol of ethanol and 4 mL of benzene were added into a 25 mL 3-neck flask equipped with a water knockout drum, a reflux condenser and a magnetic stirrer with heating. The mixture was heated to reflux for 10 hours. Then the reaction was cooled to room temperature. The reaction mixture was evaporated to remove solvents before washed with a suitable amount of acetic ether, filtered, filtrate was collected and evaporated to remove solvents to obtain a yellow oil (Intermediate I).

0.01 mol of 1-(but-3-ynyl)-2,3,3-trimethyl-3H-indolium bromide, 20 ml of ethanol and 4 mL of trithylamine were added into a 50 mL 3-neck flask equipped with a reflux condenser and a magnetic stirrer with heating. The mixture was stirred and heated to 70° C. for 30 minutes before 0.015 mol of the yellow oil was added. The mixture was further heated for 30 minutes. Then the reaction was stopped and cooled to room temperature. The reaction mixture was evaporated to remove solvents before washed with absolute ether, purified by silica gel column chromatography eluting with a gradient of ethyl acetate: methanol=100:0→100:20 to obtain a product (Intermediate II).

0.005 mol of the Intermediate II and 20 ml of ethanol were added into a 25 mL 3-neck flask equipped with a reflux condenser and a magnetic stirrer with heating. The mixture was heated to reflux before 0.1 mL 40% sodium hydroxide solution was added in reflux status and then further heated for 10 minutes. The reaction was stopped and the mixture was adjusted to neutral pH before evaporated to remove solvents to obtain a solid product. The solid product, 0.005 mol of 1-(2-allyl)-2,3,3-trimethylindole bromide, 6 mL of toluene, 4 mL of n-butyl alcohol and 4 mL of pyridine which were used as solvents were added together into a 25 mL 3-neck flask, and the mixture was stirred and heated to reflux in an argon atmosphere for 6 hours. Then the reaction was stopped and cooled to room temperature. The product was precipitated out by adding an excess amount of ethyl ether, filtered, washed with a suitable amount of ethyl ether, and dried to obtain a dark blue solid. The dark blue solid was purified by silica gel column chromatography eluting with a gradient of ethyl acetate:methanol=100:0→100:20. The blue fractions were collected and the solvents therein were removed by rotary evaporation. The resulting residue was dried in a vacuum drying chamber at 45° C. for 24 hours to afford the title compound as a blue solid having a golden metallic luster, with a yield of 20%.

MS (EI) $C_{33}H_{33}BrN_2O_2$ m/z: 489.6 [M-Br]$^+$.

Example 8

Synthesis of Other Compounds

| Name of compound | Synthesis | MS (EI) |
|---|---|---|
| Compound 4 | Referring to the synthesis of Compound 1 | MS (EI) $C_{36}H_{41}BrN_2O_2$ m/z: 533.32[M-Br]$^+$. |
| Compound 5 | Referring to the synthesis of Compound 1 | MS (EI) $C_{38}H_{45}BrN_2O_2$ m/z: 561.35[M-Br]$^+$. |
| Compound 6 | Referring to the synthesis of Compound 1 | MS (EI) $C_{40}H_{49}BrN_2O_2$ m/z: 589.38[M-Br]$^+$. |
| Compound 7 | Referring to the synthesis of Compound 1 | MS (EI) $C_{42}H_{53}BrN_2O_2$ m/z: 617.41[M-Br]$^+$. |
| Compound 9 | Referring to the synthesis of Compound 8 | MS (EI) $C_{30}H_{29}BrN_2O_2S_2$ m/z: 533.32[M-Br]$^+$. |
| Compound 12 | Referring to the synthesis of Compound 8 | MS (EI) $C_{36}H_{37}BrN_2O_2$ m/z: 529.28[M-Br]$^+$. |
| Compound 13 | Referring to the synthesis of Compound 8 | MS (EI) $C_{38}H_{41}BrN_2O_2$ m/z: 557.32[M-Br]$^+$. |
| Compound 14 | Referring to the synthesis of Compound 8 | MS (EI) $C_{26}H_{17}BrN_2O_2$ m/z: 421.12[M-Br]$^+$. |
| Compound 15 | Referring to the synthesis of Compound 8 | MS (EI) $C_{28}H_{21}BrN_2O_2S_2$ m/z: 481.10[M-Br]$^+$. |
| Compound 16 | Referring to the synthesis of Compound 11 | MS (EI) $C_{32}H_{27}KN_2O_8S_2$ m/z: 631.12[M-2K]$^+$. |
| Compound 17 | Referring to the synthesis of Compound 2 | MS (EI) $C_{34}H_{35}KN_2O_8S_2$ m/z: 663.18[M-2K]$^+$. |
| Compound 18 | Referring to the synthesis of Compound 2 | MS (EI) $C_{34}H_{37}IN_2O_2$ m/z: 505.28[M-I]$^+$. |
| Compound 19 | Referring to the synthesis of Compound 2 | MS (EI) $C_{36}H_{41}IN_2O_2$ m/z: 533.32[M-I]$^+$. |
| Compound 20 | Referring to the synthesis of Compound 3 | MS (EI) $C_{38}H_{45}BrN_2O_4$ m/z: 593.34[M-Br]$^+$. |
| Compound 21 | Referring to the synthesis of Compound 3 | MS (EI) $C_{42}H_{41}BrN_2O_4$ m/z: 605.32[M-Br]$^+$. |
| Compound 22 | Referring to the synthesis of Compound 3 | MS (EI) $C_{44}H_{45}BrN_2O_4$ m/z: 665.34[M-Br]$^+$. |

Example 9

Determination of the molar extinction coefficient of the Compound 1, 10 and 23 in ethanol solution.

Provided an ethanol solution containing $1 \times 10^{-5}$ mol/L dissolved Compound 1, 10 and 23, 50 μL of the solution were each diluted to 3 mL by ethanol. The dilution was placed in a cuvette with 1 cm optical path and absorbance value was detected respectively using an UV-mini-1240 UV-Vis Spectrophotometer. Each sample was tested three times in parallel, the molar extinction coefficient was calculated according to the Lambert-Beer's law and the average was taken. $\epsilon 1 = 1.23 \times 10^5$, $\epsilon 10 = 1.07 \times 10^5$, $\epsilon 23 = 0.63 \times 10^5$ (25° C., ethanol solution).

The data indicate that dyes according to the present disclosure have bigger molar extinction coefficient and better sensibility when they are used in a test.

Example 10

The Composition 10 according to the present disclosure has the following components:

| | |
|---|---|
| Fluorescent dye (compound 1) | 3 mg/L |
| Citric acid | 2.5 g/L |
| Sodium Citrate | 0.88 g/L |
| Dodecyltrimethylammonium chloride | 0.6 g/L |

-continued

| | |
|---|---|
| 4-methoxyphenol | 0.2 g/L |
| pH value | 3.8 | wherein the fluorescent dye has the following structure:

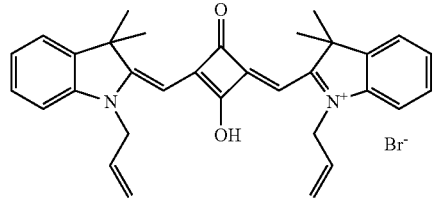

Figure 2:
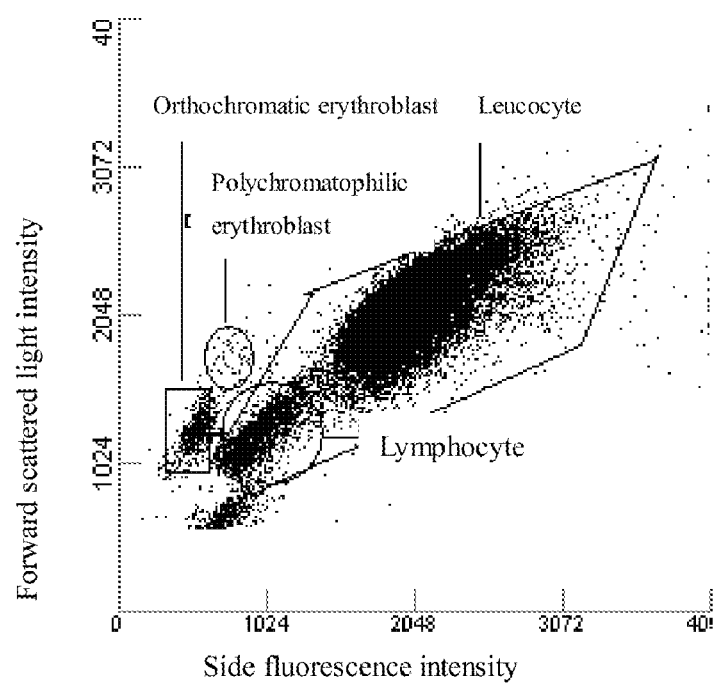
FIG. 2 is a cell differentiation scattergram of Example 10, wherein the X-axis shows side fluorescence intensity and the Y-axis shows forward scattered light intensity.

A blood sample containing erythroblasts was added to Composition 10, mixed for 4.8 seconds while the temperature was kept at 42° C. The ratio between the blood sample and the composition was 1:50. Erythroblasts were analyzed by the laser flow cytometry method (excitation light source: red semiconductor laser, excitation wavelength 635 nm). Forward scattered light at the detection angle of 1-10° and side fluorescence at the detection angle of 90° were detected. In term of analysis of information of forward scattered light and side fluorescence, erythroblasts were differentiated from leucocytes and at the same time lymphocytes were differentiated from other leucocytes. The scattergram result is shown in FIG. 2. The ratio of erythroblasts was 1.89% and that of lymphocytes was 6.93%. The same sample was determined by the Wright-Giemsa staining method recommended by the International Committee for Standardization of Hematology (ICSH). The ratio of erythroblasts was 2.0% (2 erythroblasts/100 leucocytes) and that of lymphocytes was 7.5% (7.5 lymphocytes/100 leucocytes).

Example 11

The Composition 11 according to the present disclosure has the following components:

| | |
|---|---|
| Fluorescent dye (compound 15) | 10 mg/L |
| Citric acid | 2.5 g/L |
| Sodium Citrate | 0.88 g/L |
| polyoxyethylene(23)cetyl ether | 0.4 g/L |
| pH value | 3.8 | wherein the fluorescent dye has the following structure:

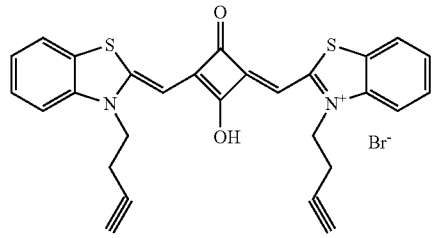

Figure 3:
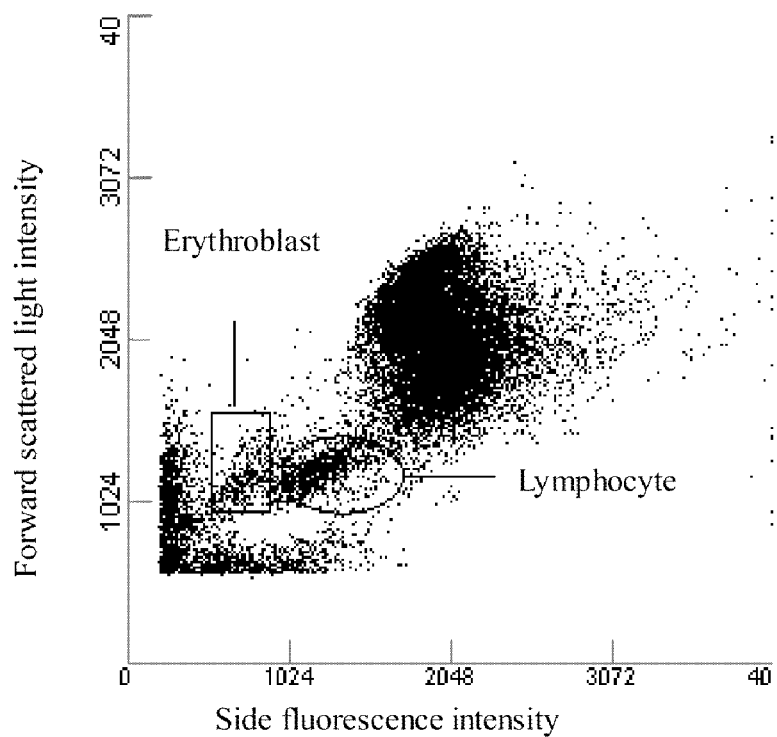
FIG. 3 is a cell differentiation scattergram of Example 11, wherein the X-axis shows side fluorescence intensity and the Y-axis shows forward scattered light intensity.

20 μl of blood sample containing erythroblasts was added into 1 ml of Composition 11, mixed for 6 seconds while the temperature was kept at 42° C. Erythroblasts and lymphocytes were analyzed using the laser flow cytometry method (excitation light source: red semiconductor laser, excitation wavelength 635 nm). Forward scattered light at the detection angle of 1-10° and side fluorescence at the detection angle of 90° were detected. In term of analysis of information of forward scattered light and side fluorescence, erythroblasts were differentiated from leucocytes and lymphocytes were simultaneously differentiated from other leucocytes. The scattergram result is shown in FIG. 3, wherein erythroblasts and lymphocytes are shown as independent groups and separate from other leucocytes. The ratio of erythroblasts was 2.62% and that of lymphocytes was 7.39%. The same sample was determined by the Wright-Giemsa staining method recommended by the International Committee for Standardization of Hematology (ICSH). The ratio of erythroblasts was 3.0% and that of lymphocytes was 7.5%.

Example 12

The Composition 12 according to the present disclosure has the following components:

| | |
|---|---|
| Fluorescent dye (compound 2) | 5 g/L |
| Sodium salicylate | 2.0 g/L |
| Citric acid | 1.6 g/L |
| Dodecyltrimethylammonium bromide | 0.4 g/L |
| 4-methoxyphenol | 0.3 g/L |
| Adjust pH value with NaOH | 3.7 | wherein the fluorescent dye has the following structure:

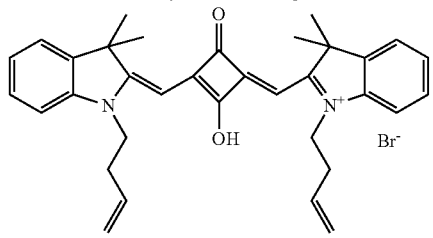

Figure 4:
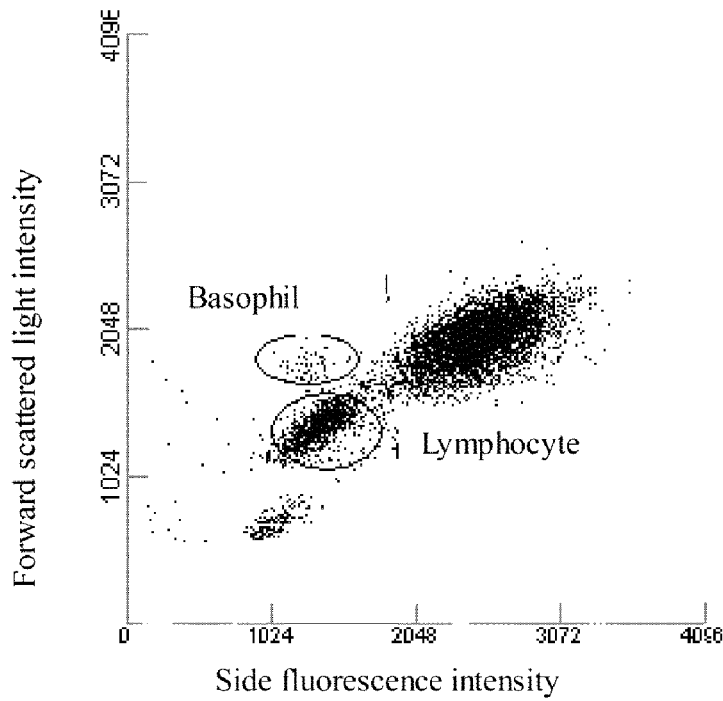
FIG. 4 is a cell differentiation scattergram of Example 12, wherein the X-axis shows side fluorescence intensity and the Y-axis shows forward scattered light intensity.

A blood sample of a normal person was added into Composition 12, mixed for 4.8 seconds while the temperature was kept at 42° C. The ratio between the blood sample and the composition was 1:50. Basophils were analyzed using the laser flow cytometry method (excitation light source red: semiconductor laser, excitation wavelength 635 nm). Forward scattered light at the detection angle of 1-10° and side fluorescence at the detection angle of 90° were detected. In term of analysis of information of forward scattered light and side fluorescence, basophils and lymphocytes were differentiated from leucocytes respectively. The scattergram result is shown in FIG. 4, wherein basophils and lymphocytes are shown as independent groups. The ratio of basophils was 0.93% and that of lymphocytes was 36.93%. The same sample was determined by the Wright-Giemsa staining method recommended by the International Committee for Standardization of Hematology (ICSH). The ratio of basophils was 1.0% and that of lymphocytes was 40.5%.

Example 13

The Composition 13 according to the present disclosure has the following components:

| | |
|---|---|
| Fluorescent dye (compound 1) | 5 mg/L |
| Sodium salicylate | 1.6 g/L |
| Citric acid | 1.47 g/L |
| Sodium Citrate | 0.88 g/L |
| Dodecyltrimethylammonium chloride | 0.4 g/L |

| | |
|---|---|
| 4-methoxyphenol | 0.1 g/L |
| pH value | 3.7 | wherein the fluorescent dye has the following structure:

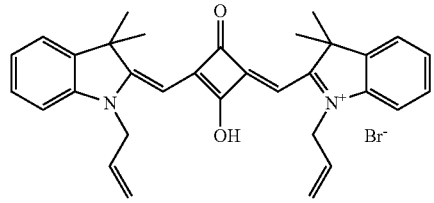

Figure 5:
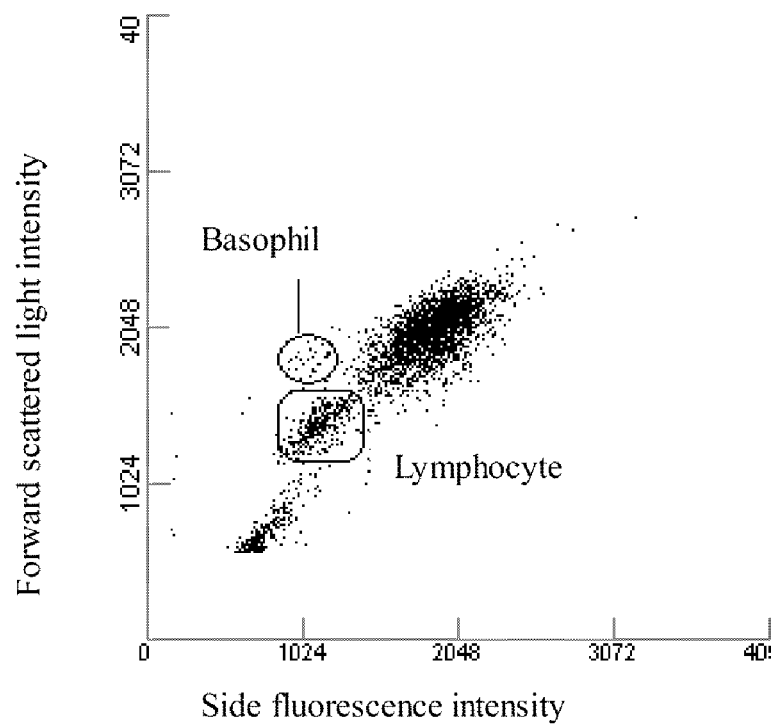
FIG. 5 is a cell differentiation scattergram of Example 13, wherein the X-axis shows side fluorescence intensity and the Y-axis shows forward scattered light intensity.

20 μl of blood sample containing higher percentage of basophils was added into 1 ml of the Composition 13, mixed for 4.8 seconds while the temperature was kept at 42° C. Lymphocytes were analyzed using the laser flow cytometry method (excitation light source: red semiconductor laser, excitation wavelength 635 nm). Forward scattered light at the detection angle of 1-10° and side fluorescence at the detection angle of 90° were detected. In term of analysis of information of forward scattered light and side fluorescence, lymphocytes and basophils were differentiated from leucocytes. The scattergram result is shown in FIG. 5, wherein lymphocytes and basophils are shown as independent groups. The ratio of lymphocytes was 10.8% and that of basophils was 1.2%. The same sample was determined by the Wright-Giemsa staining method recommended by the International Committee for Standardization of Hematology (ICSH). The ratio of lymphocytes was 9.5% and that of basophils was 1.0%.

Example 14

The Composition 14 according to the present disclosure has the following components:

| | |
|---|---|
| Fluorescent dye (compound 4) | 5 mg/L |
| Sodium benzoate | 1.6 g/L |
| Citric acid | 1.47 g/L |
| Sodium Citrate | 0.8 g/L |
| Dodecyltrimethylammonium chloride | 0.6 g/L |
| polyoxyethylene(25)cetyl ether | 0.1 g/L |
| pH value | 3.7 | wherein the fluorescent dye has the following structure:

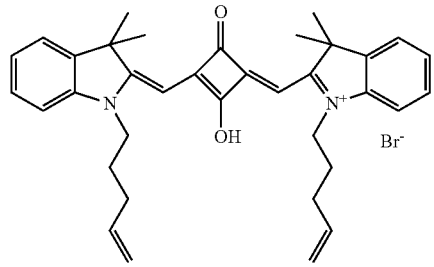

Figure 6:
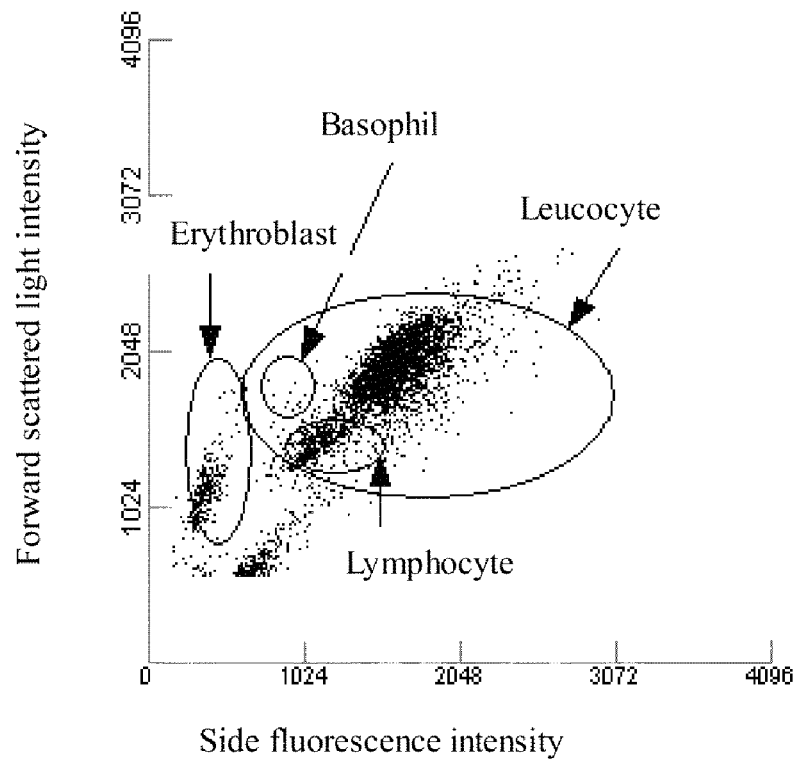
FIG. 6 is a cell differentiation scattergram of Example 14, wherein the X-axis shows side fluorescence intensity and the Y-axis shows forward scattered light intensity.

20 μl of clinical blood sample was added into 1 ml of Composition 14, mixed for 4.8 seconds while the temperature was kept at 42° C. Erythroblasts, basophils and lymphocytes were analyzed using the laser flow cytometry method (excitation light source: red semiconductor laser, excitation wavelength 635 nm). Forward scattered light at the detection angle of 1-10° and side fluorescence at the detection angle of 90° were detected. In term of analysis of information of forward scattered light and side fluorescence, erythroblasts were differentiated from leucocytes, lymphocytes and basophils were differentiated from other leucocytes. The scattergram result is shown in FIG. 6, wherein erythroblasts, basophils and lymphocytes are shown as independent groups. The ratio of erythroblasts was 8.07%, that of basophils was 0.33% and that of lymphocytes was 12.9%. The same sample was determined by the Wright-Giemsa staining method recommended by the International Committee for Standardization of Hematology (ICSH). The ratio of erythroblast was 8.5%, that of basophils was 0 and that of lymphocytes was 13.5%. When erythroblasts or subgroups of leucocytes are counted by artificial microscopy of staining method, 100 leucocytes are counted for the calculation of their final percentage. Thus, when the percentage of erythroblasts or basophils is less than 1%, the final result is likely to be 0. From this point, the method of the present disclosure may give more accurate results for various cells, particularly, those cells present in a small amount in a normal blood sample, such as erythroblasts and basophils.

Example 15

The Composition 15 according to the present disclosure has the following components:

| | |
|---|---|
| Fluorescent dye (compound 1) | 2 mg/L |
| Sodium benzoate | 1.8 g/L |
| Citric acid | 2.5 g/L |
| Sodium Citrate | 0.88 g/L |
| decyltrimethylammonium bromide | 0.2 g/L |
| polyoxyethylene(25)cetyl ether | 0.1 g/L |
| pH value | 3.8 | wherein the fluorescent dye has the following structure:

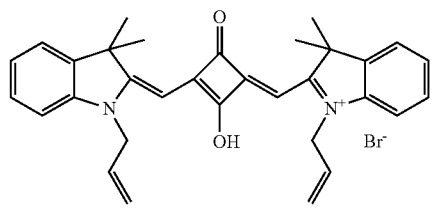

Figure 7:
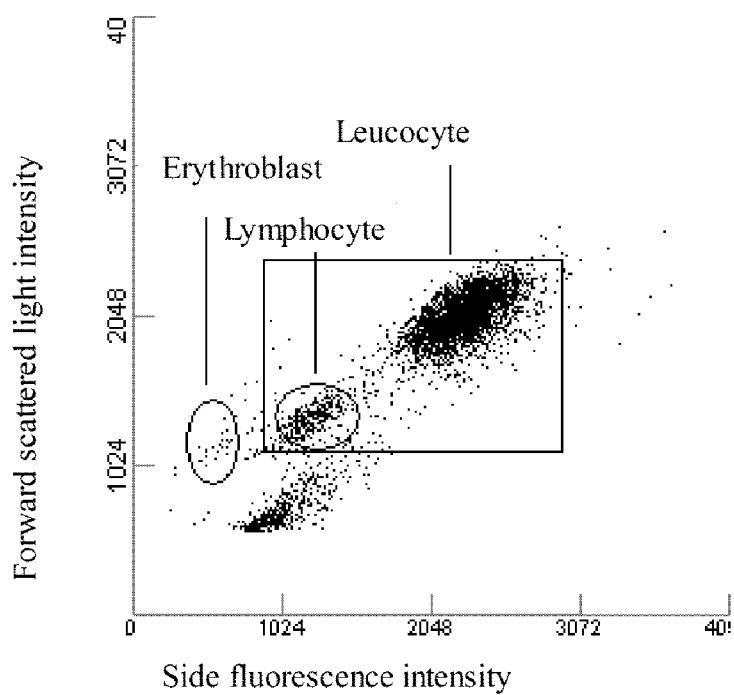
FIG. 7 is a cell differentiation scattergram of Example 15, wherein the X-axis shows side fluorescence intensity and the Y-axis shows forward scattered light intensity.

20 μl of blood sample containing erythroblasts was added into 1 ml of Composition 15, mixed for 4.8 seconds while the temperature was kept at 42° C. Erythroblasts were analyzed using the laser flow cytometry method (excitation light source: red semiconductor laser, excitation wavelength 635 nm). Forward scattered light at the detection angle of 1-10° and side fluorescence at the detection angle of 90° were detected. In term of analysis of information of forward scattered light and side fluorescence, erythroblasts were differentiated from leucocytes and lymphocytes were simultaneously differentiated from other leucocytes. The scattergram result is shown in FIG. 7, wherein erythroblasts and lymphocytes are shown as independent groups. The ratio of erythroblasts was 0.87% and that of lymphocytes was 8.3%. The same sample was determined by the Wright-Giemsa staining method recommended by the International Committee for Standardization of Hematology (ICSH). The ratio of erythroblasts was 1.0% and that of lymphocytes was 7.5%.

Example 16

The Composition 16 according to the present disclosure has the following components:

| | |
|---|---|
| Fluorescent dye (compound 10) | 5 mg/L |
| Sodium salicylate | 2.0 g/L |
| Citric acid | 1.5 g/L |
| myristyltrimethylammonium chloride | 0.1 g/L |
| polyoxyethylene(25)cetyl ether | 0.1 g/L |
| Adjust pH value with NaOH | 3.5 | wherein the fluorescent dye has the following structure:

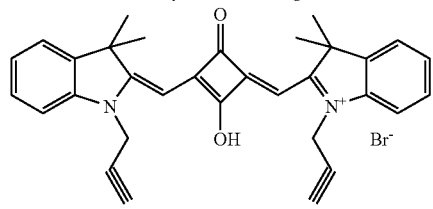

Figure 8:
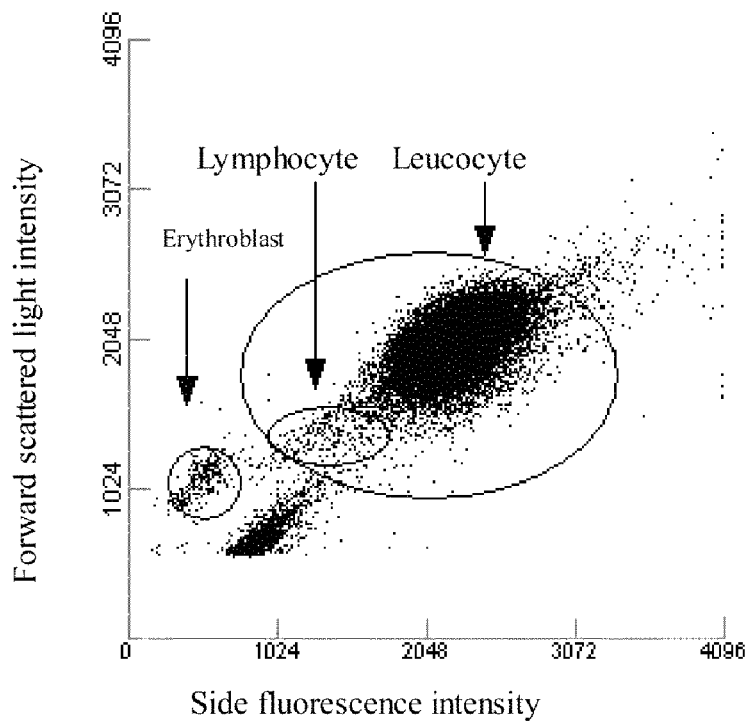
FIG. 8 is a cell differentiation scattergram of Example 16, wherein the X-axis shows side fluorescence intensity and the Y-axis shows forward scattered light intensity.

5 μl of blood sample containing erythroblasts was added into 1 ml of Composition 16 and mixed for 6 seconds while the temperature was kept at 42° C. Erythroblasts and lymphocytes were analyzed using the laser flow cytometry method (excitation light source: red semiconductor laser, excitation wavelength 635 nm). Forward scattered light at the detection angle of 1-10° and side fluorescence at the detection angle of 90° were detected. In term of analysis of information of forward scattered light and side fluorescence, erythroblasts were differentiated from whole leucocytes, and lymphocytes were simultaneously differentiated from other leucocytes. The scattergram result is shown in FIG. 8, wherein erythroblasts and lymphocytes are shown as independent groups. The ratio of erythroblasts was 1.31% and that of lymphocytes was 1.8%. The same sample was determined by the Wright-Giemsa staining method recommended by the International Committee for Standardization of Hematology (ICSH). The ratio of erythroblast was 1.5% and that of lymphocytes was 2.0%.

Example 17

The Composition 17 according to the present disclosure has the following components:

| | |
|---|---|
| Fluorescent dye (compound 2) | 1.5 mg/L |
| Sodium salicylate | 0.8 g/L |
| Citric acid | 1.47 g/L |
| Sodium Citrate | 0.88 g/L |
| Dodecyltrimethylammonium bromide | 0.4 g/L |
| glucose | 10 g/L |
| pH value | 3.8 | wherein the fluorescent dye has the following structure:

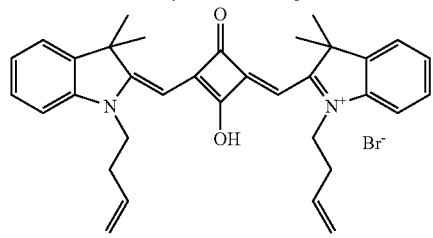

Figure 9:
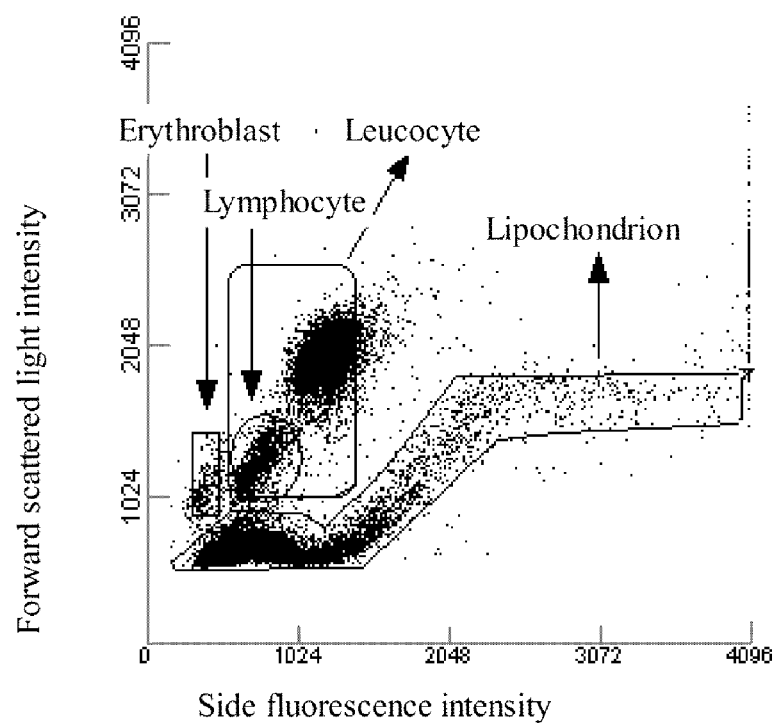
FIG. 9 is a cell differentiation scattergram of Example 17, wherein the X-axis shows side fluorescence intensity and the Y-axis shows forward scattered light intensity.

20 μl of clinical blood sample was added into 1 ml of Composition 17, mixed for 4.8 seconds while the temperature was kept at 42° C. Erythroblasts and lymphocytes were analyzed using the laser flow cytometry method (excitation light source: red semiconductor laser, excitation wavelength 635 nm). Forward scattered light at the detection angle of 1-10° and side fluorescence at the detection angle of 90° were detected. In term of analysis of information of forward scattered light and side fluorescence, erythroblasts were differentiated from whole leucocytes, and lymphocytes were simultaneously differentiated from other leucocytes. The scattergram result is shown in FIG. 9, wherein erythroblasts and lymphocytes are shown as independent groups. The ratio of erythroblasts was 3.67% and that of lymphocytes was 18.87%. The same sample was determined by the Wright-Giemsa staining method recommended by the International Committee for Standardization of Hematology (ICSH). The ratio of erythroblast was 3.5% and that of lymphocytes was 19%. The irregular area in the bottom of the scattergram was proven to be lipochondrion by artificial microscopy. Because the lipochondrion of this sample are different in size, which creates different forward scattered light signals, at the same time, the lipochondrion bring interference to side fluorescence, and are shown as an irregular shape in the scattergram. However, it is also shown in the scattergram that lipochondrion does not completely interfere with the differentiation of erythroblasts, lymphocytes, basophils and the counting of total leucocytes. It means that lipochondriom does not interfere with analysis of a blood sample using the method and reagent of the present disclosure.

Example 18

The Composition 18 according to the present disclosure has the following components:

| | |
|---|---|
| Fluorescent dye (compound 23) | 6 mg/L |
| Sodium salicylate | 2.5 g/L |
| Citric acid | 1.47 g/L |
| Sodium Citrate | 0.98 g/L |
| Dodecyltrimethylammonium chloride | 0.5 g/L |
| polyoxyethylene(25)cetyl ether | 0.12 g/L |
| pH value | 3.8 | wherein the fluorescent dye has the following structure:

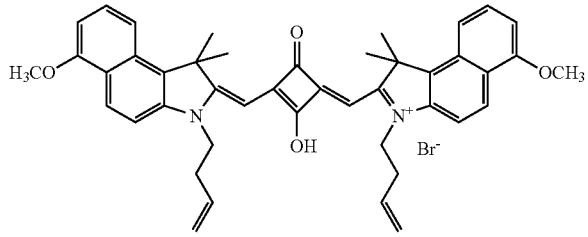

Figure 10:
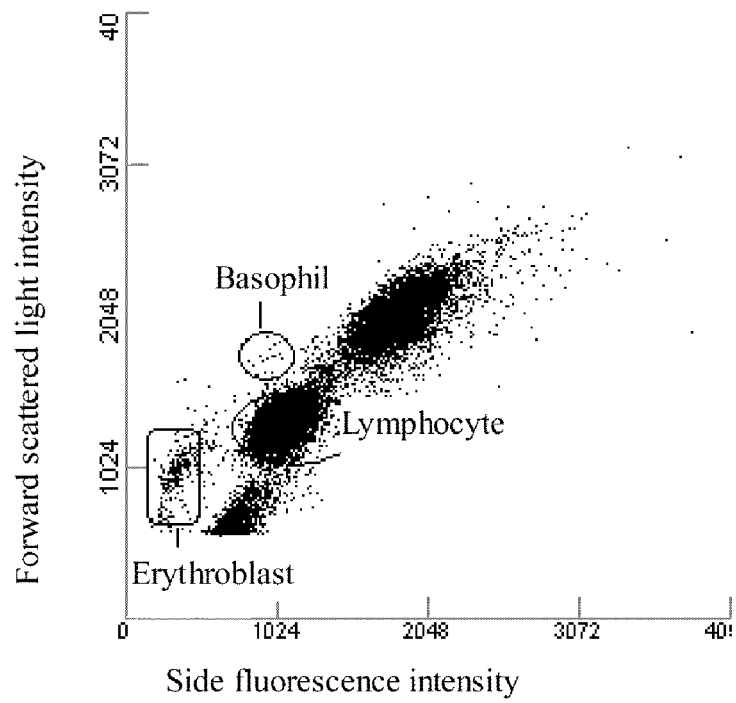
FIG. 10 is a cell differentiation scattergram of the Example 18, wherein the X-axis shows side fluorescence intensity and the Y-axis shows forward scattered light intensity.

5 μl of blood sample containing erythroblasts was added into 1 ml of the Composition 18, mixed for 6 seconds while the temperature was kept at 44° C. Erythroblasts, lymphocytes and basophils were analyzed using the laser flow cytometry method (excitation light source: red semiconductor laser, excitation wavelength 635 nm). Forward scattered light at the detection angle of 1-10° and side fluorescence at the detection angle of 90° were detected. In term of analysis of information of forward scattered light and side fluorescence, erythroblasts were differentiated from the whole leucocytes, and basophils and lymphocytes were simultaneously differentiated from other leucocytes. The scattergram result is shown in FIG. 10, wherein erythroblasts are shown as an independent group at the bottom-left of the scattergram and basophils and lymphocytes are shown as independent groups. The ratio of erythroblasts was 1.41%, that of basophils was 0.13% and that of lymphocytes was 66.1%. The same sample was determined by the Wright-Giemsa staining method recommended by the International Committee for Standardization of Hematology (ICSH). The ratio of erythroblast was 2.0%, that of basophils was 0% and that of lymphocytes was 64.0%.

Example 19

The Composition 19 according to the present disclosure has the following components:

| | |
|---|---|
| Fluorescent dye (compound 5) | 3 mg/L |
| Sodium salicylate | 0.8 g/L |
| Citric acid | 1.47 g/L |
| Sodium Citrate | 0.88 g/L |
| Dodecyltrimethylammonium bromide | 0.4 g/L |
| polyoxyethylene(30)cetyl ether | 0.1 g/L |
| pH value | 3.7 | wherein the fluorescent dye has the following structure:

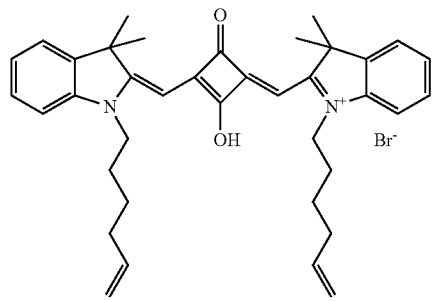

Figure 11:
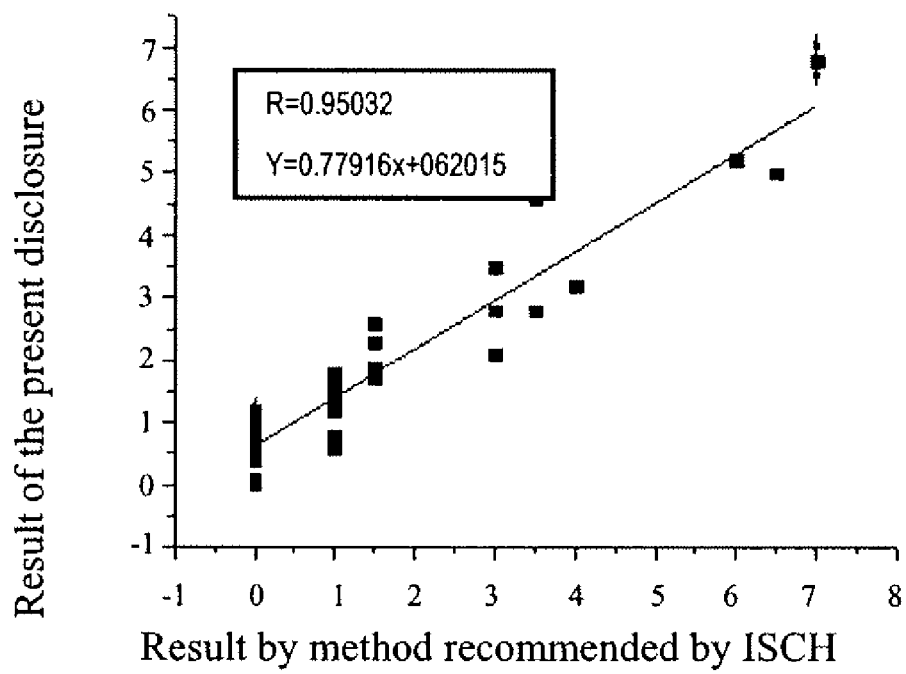
FIG. 11 is a graph which shows a correlation between the percentage results of erythroblasts obtained by an analysis method of the present disclosure and those obtained by a traditional method in Example 19.
Figure 12:
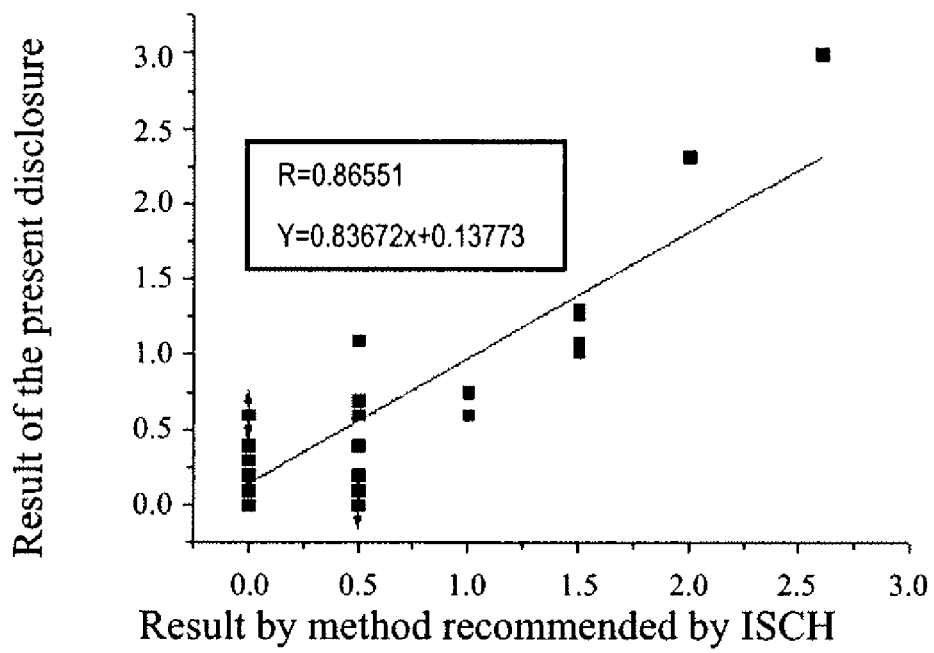
FIG. 12 is a graph which shows a correlation between the percentage results of basophils obtained by an analysis method of the present disclosure and those obtained by a traditional method in Example 19.
Figure 13:
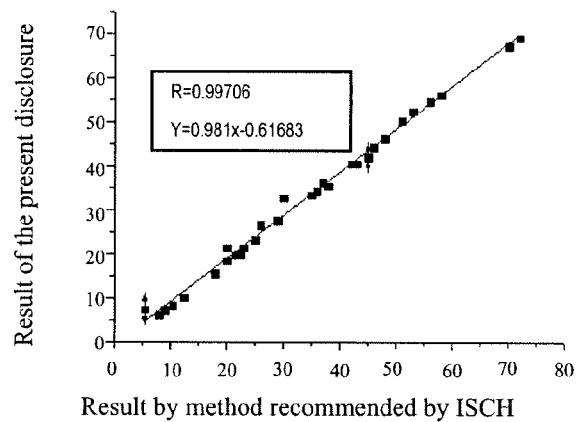
FIG. 13 is a graph which shows a correlation between the percentage results of lymphocytes obtained by an analysis method of the present disclosure and those obtained by a traditional method in Example 19.
Figure 14A:
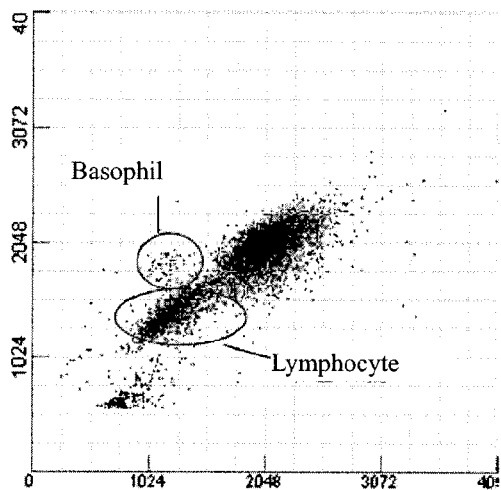
FIG. 14A is a cell differentiation scattergram of Example 20 using Reagent A, wherein the X-axis shows side fluorescence intensity and the Y-axis shows forward scattered light intensity.
Figure 14B:
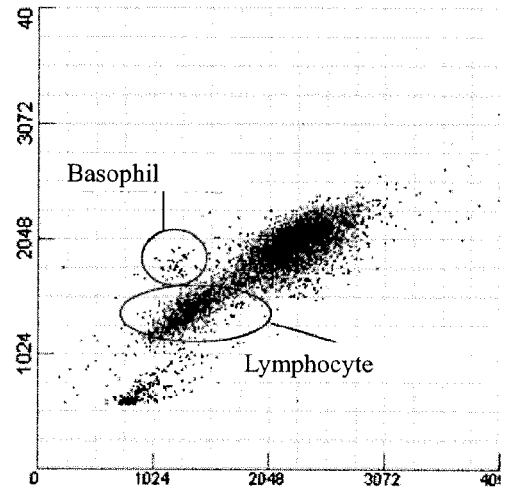
FIG. 14B is a cell differentiation scattergram of Example 20 using Reagent B, wherein the X-axis shows side fluorescence intensity and the Y-axis shows forward scattered light intensity.

Thirty (30) clinical samples were taken, which were respectively mixed with Composition 19 at the ratio of 1:50 for 4.8 seconds while the temperature was kept at 42° C. Erythroblasts, lymphocytes and basophils were analyzed using the laser flow cytometry method (excitation light source: red semiconductor laser, excitation wavelength 635 nm). Forward scattered light at the detection angle of 1-10° and side fluorescence at the detection angle of 90° were detected. In term of analysis of information of forward scattered light and side fluorescence, cells of the blood samples were differentiated and counted respectively. These thirty results obtained were compared with that obtained by artificial microscopy of the Wright-Giemsa staining method recommended by the International Committee for Standardization of Hematology (ICSH). The comparison results are: the correlation of percentage of erythroblasts as shown in FIG. 11, the correlation of percentage of basophils as shown in FIG. 12, the correlation of percentage of lymphocytes as shown in FIG. 13; correlation coefficient of NRBC % R=0.95032, correlation coefficient of Baso % R=0.86551, correlation coefficient of Lym % R=0.99706.

Example 20

The compositions of this example have the following components:

| | Reagent A<br>Compound 2 | Reagent B<br>Control compound |
|---|---|---|
| Fluorescent dye | 2 mg/L | 10 mg/L |
| Sodium salicylate | 2.0 g/L | 2.0 g/L |
| Citric acid | 1.6 g/L | 1.6 g/L |
| Dodecyltrimethylammonium chloride | 0.6 g/L | 0.6 g/L |
| 4-methoxyphenol | 0.2 g/L | 0.2 g/L |
| Adjust the pH value of the reagent to about 3.8 with NaOH | | | wherein the Compound 2 has the following structure:

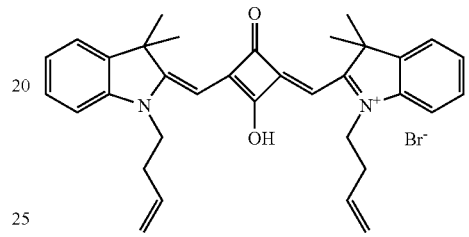

Control compound has the following structure and, its synthesis is referred to in U.S. application Ser. No. 12/607,614:

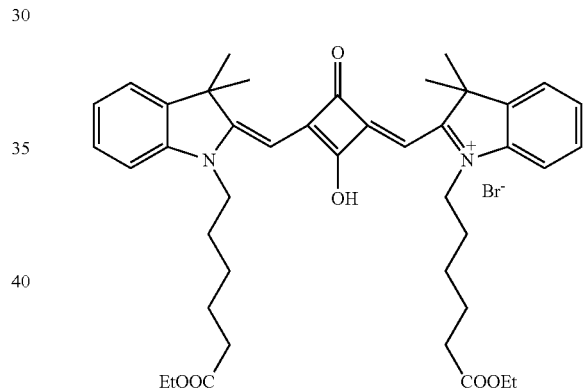

A blood sample of normal person was split into two aliquots, and were added into Reagent A and Reagent B respectively, mixed for 4.8 seconds while the temperature was kept at 42° C. and, the ratio between the blood sample and the composition was 1:50. The blood sample was analyzed using the laser flow cytometry method (excitation light source: red semiconductor laser, excitation wavelength 635 nm). Forward scattered light at the detection angle of 1-10° and side fluorescence at the detection angle of 90° were detected to achieve scattergram 14A and 14B. By comparing these two scattergram, it is shown that their cellar fluorescent strength and differentiation effect are similar. It means that compounds of the present disclosure have higher fluorescence quantum efficiency so that the similar differentiation effect can be achieved by using less amount of fluorescent dye.

Although the present disclosure has been illustrated by way of the above embodiments and particular examples thereof, it will be appreciated by those skilled in the art that various changes, alterations and modifications may be made to the present disclosure without departing from the spirit and scope of the present disclosure as claimed.

The invention claimed is:
1. A compound having the general formula I:

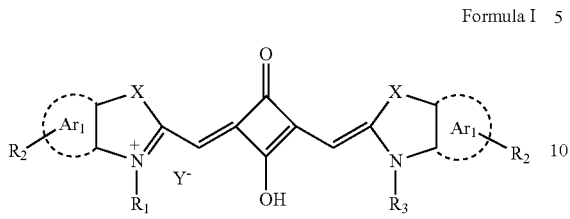

Formula I wherein
Ar$_1$ is a benzene ring;
X is selected from at least one of the following: —O—, —S—, and

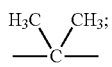

R$_1$ and R$_3$ are independently selected from C$_{3-20}$ alkenyl or C$_{3-20}$ alkynyl;
R$_2$ is selected from at least one of the following: hydrogen, carboxy, sulphonyl, C$_{1-20}$ saturated or unsaturated alkyl or C$_{1-20}$ saturated or unsaturated alkoxyl; and
Y$^-$ is an anion.

2. The compound according to claim 1, wherein X is selected from —S—, or

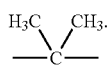

3. The compound according to claim 1, wherein R$_1$ and R$_3$ are independently selected from C$_{3-18}$ alkenyl or C$_{3-18}$ alkynyl.

4. The compound according to claim 1, wherein R$_1$ and R$_3$ are independently selected from C$_{3-8}$ alkenyl or C$_{3-8}$ alkynyl.

5. The compound according to claim 1, wherein R$_2$ is selected from hydrogen, carboxy, sulphonyl, C$_{1-12}$ saturated or unsaturated alkyl or C$_{1-12}$ saturated or unsaturated alkoxyl.

6. The compound according to claim 1, wherein R$_2$ is selected from hydrogen, carboxy, sulphonyl, C$_{1-8}$ saturated or unsaturated alkyl or C$_{1-8}$ saturated or unsaturated alkoxyl.

7. The compound according to claim 1, wherein Y$^-$ is selected from at least one of the following: Cl$^-$, Br$^-$, I$^-$, ClO$_4^-$, PF$_6^-$ and p-CH$_3$C$_6$H$_4$—SO$_3^-$.

8. The compound according to claim 1, wherein said compound is selected from:

Compound 1

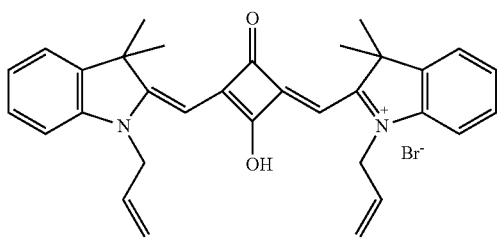

Compound 2

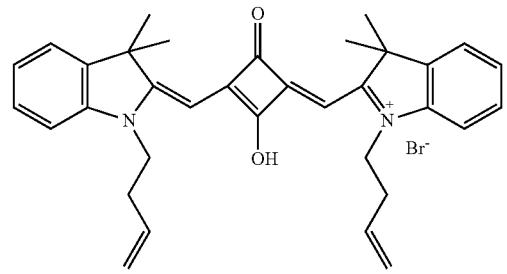

Compound 3

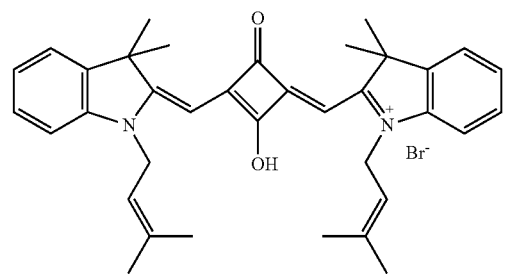

Compound 4

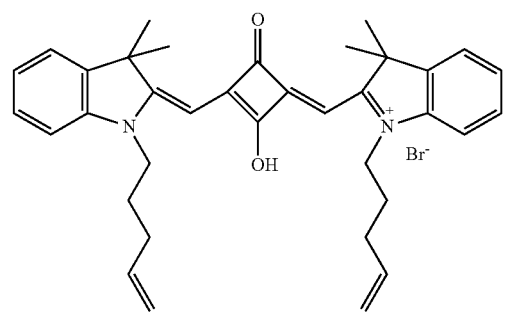

Compound 5

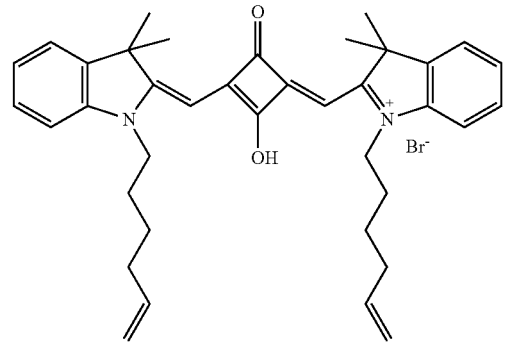

Compound 6
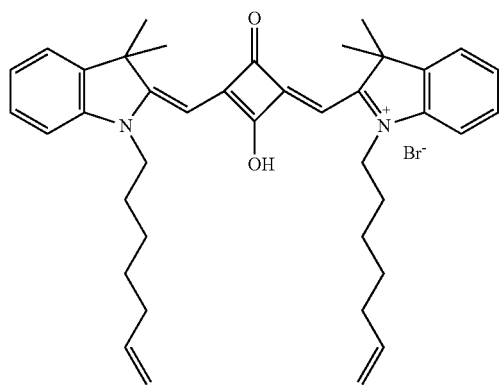
Compound 7
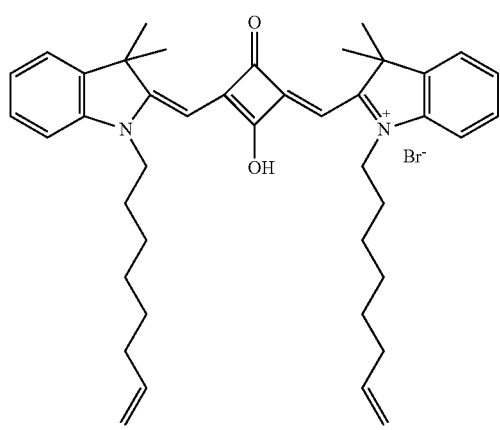
Compound 8
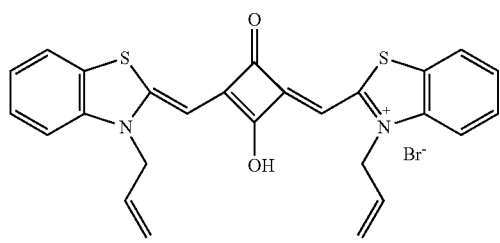
Compound 9
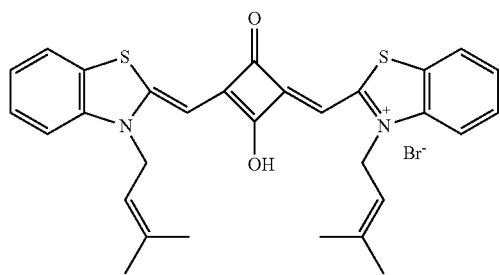
Compound 10
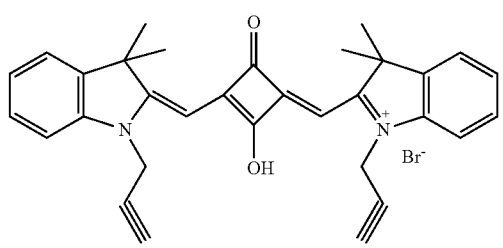
Compound 11
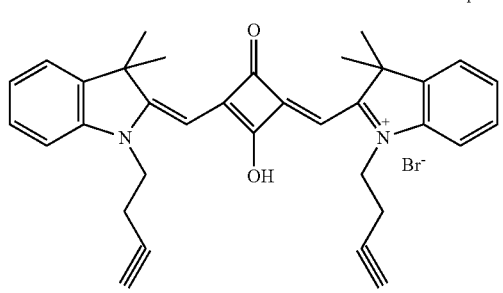
Compound 12
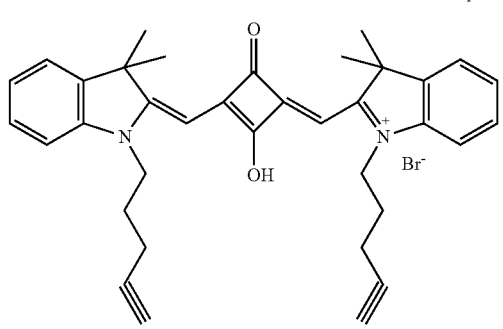
Compound 13
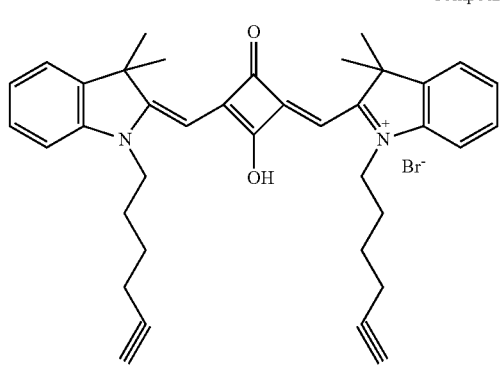
Compound 14
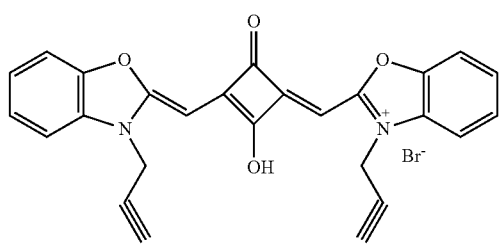

Compound 15

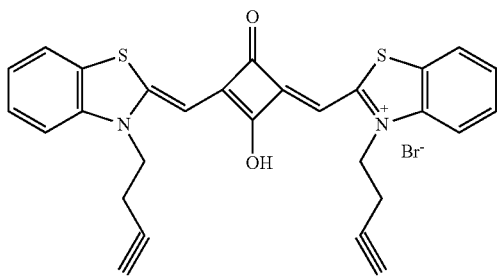

Compound 18

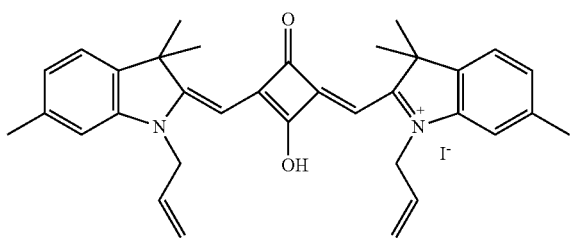

Compound 19

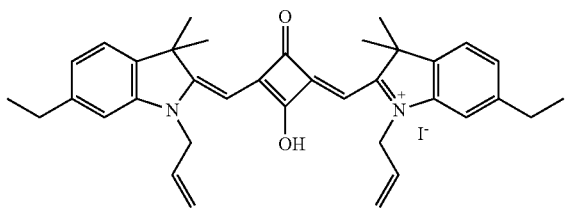

Compound 20

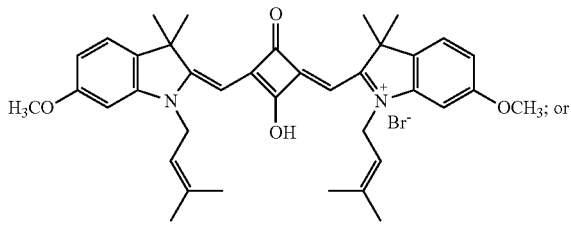

Compound 23

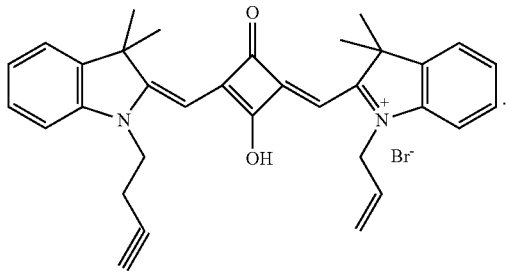

9. A conjugate comprising the compound according to claim 1.

10. A composition, said composition comprising:
(i) a compound according to formula I

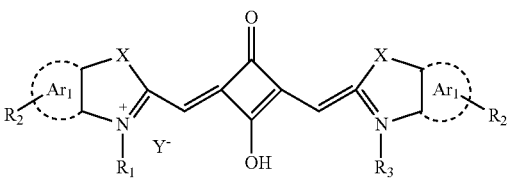

Formula I wherein
Ar$_1$ is an aromatic ring;
X is selected from at least one of the following: —O—, —S—, and

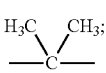

R$_1$ and R$_3$ are independently selected from C$_{3-20}$ alkenyl or C$_{3-20}$ alkynyl;
R$_2$ is selected from at least one of the following: hydrogen, carboxy, sulphonyl, C$_{1-20}$ saturated or unsaturated alkyl or C$_{1-20}$ saturated or unsaturated alkoxyl;
Y$^-$ is an anion,
or a conjugate thereof, and
(ii) at least one surfactant selected from cationic surfactants or nonionic surfactants, wherein said cationic surfactants are quaternary ammonium salt-type cationic surfactants having the following general formula II:

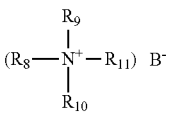

Formula II wherein
R$_8$ is alkyl or alkenyl having 6 to 14 carbon atoms;
R$_9$ and R$_{10}$ are independently selected from C$_{1-4}$ alkyl or C$_{2-4}$ alkenyl;
R$_{11}$ is selected from C$_{1-4}$ alkyl, C$_{2-4}$ alkenyl or benzyl; and
B is a halide ion, and
wherein said nonionic surfactants are polyoxyethylene-type nonionic surfactants having the general formula III:

R$_A$-R$_B$—(CH$_2$CH$_2$O)$_n$—H      Formula III wherein
R$_A$ is alkyl or alkenyl having 8 to 23 carbon atoms;
R$_B$ is selected from —O—,

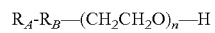

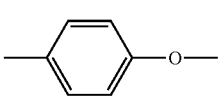

or —COO—; and
n is an integer of 8-30.

11. The composition according to claim 10, wherein $R_8$ is selected from at least one of the following: hexyl, octyl, decyl, dodecyl and myristyl group.

12. The composition according to claim 10, wherein $R_8$ is selected from at least one of the following: decyl, dodecyl and myristyl group.

13. The composition according to claim 10, wherein $R_9$ and $R_{10}$ are independently selected from at least one of following: methyl, ethyl, propyl, butyl and butenyl group.

14. The composition according to claim 10, wherein $R_9$ and $R_{10}$ are independently selected from at least one of following: methyl, ethyl and propyl.

15. The composition according to claim 10, wherein $R_4$ is straight alkyl selected from octyl, decyl, lauryl, tetradecyl, cetyl, or stearyl.

16. The composition according to claim 10, wherein $R_4$ is straight alkyl selected from lauryl, tetradecyl, or cetyl.

17. The composition according to claim 10, wherein said nonionic surfactant is selected from at least one of the following: octylphenylpolyoxyethylene ether, polyoxyethylene(10)cetyl ether, polyoxyethylene(23)cetyl ether, polyoxyethylene(25)cetyl ether and polyoxyethylene(30)cetyl ether.

18. The composition according to claim 10, wherein said nonionic surfactant is polyoxyethylene(30)cetyl ether.

19. The composition according to claim 10, wherein said composition further comprises an organic compound bearing an anionic group.

20. The composition according to claim 19, wherein said organic compound bearing an anionic group is selected from salicylic acid and salts thereof or benzoic acid and salts thereof.

21. The composition according to claim 10, wherein said composition optionally comprises a buffering agent, an osmotic regulating agent, a preservative or a metallo-chelate.

22. A method for preparing the composition according to claim 10, said method comprising:
dissolving components of the composition according to claim 10 into water to prepare a composition comprising a single constituent.

23. A method for preparing the composition according to claim 10, said method comprising:
dissolving the compound according to claim 10 into organic solvent and dissolving other components of the composition into water to prepare a composition comprising two or more constituents.

24. A reagent kit for identifying erythroblasts and simultaneously differentiating and counting leukocytes, wherein said kit comprises the composition according to claim 10, wherein said composition can either be a composition system comprising a single constituent or a composition system comprising two or more constituents.

25. A method for identifying erythroblasts and differentiating and counting leukocytes simultaneously, wherein said method comprises the following steps:
(a) mixing a blood sample with a composition comprising a compound according to Formula I

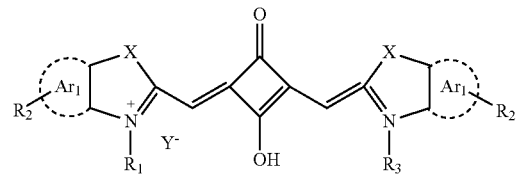

Formula I wherein $Ar_1$ is an aromatic ring;

X is selected from at least one of the following: —O—, —S—, and

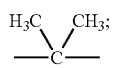

$R_1$ and $R_3$ are independently selected from $C_{3-20}$ alkenyl or $C_{3-20}$ alkynyl;

$R_2$ is selected from at least one of the following: hydrogen, carboxy, sulphonyl, $C_{1-20}$ saturated or unsaturated alkyl or $C_{1-20}$ saturated or unsaturated alkoxyl; and $Y^-$ is an anion, to form a cell suspension, wherein the compound of Formula I enters cells and combines with nucleic acids;

(b) detecting scattered light signals and fluorescence signals from cells in the cell suspension; and (c) differentiating erythroblasts and leucocytes in terms of difference of scattered light signals and fluorescence signals.

26. The method according to claim 25, further comprising:

(d) reporting a counting result of different type of cells.

27. A compound selected from:

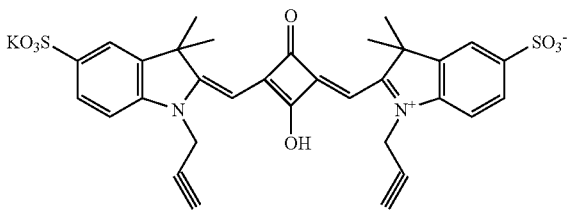

Compound 16

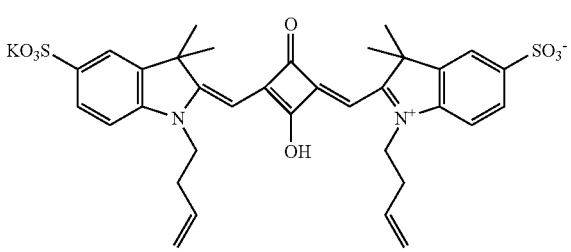

Compound 17

Compound 21
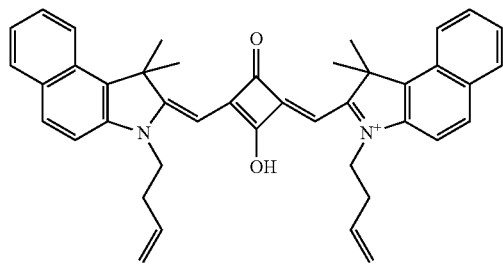
Compound 22
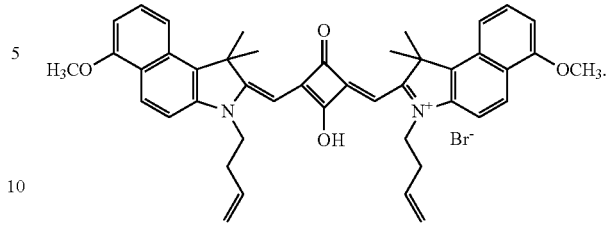
* * * * *